(12) United States Patent
Alhooshani et al.

(10) Patent No.: US 10,537,883 B2
(45) Date of Patent: Jan. 21, 2020

(54) METHOD FOR PRODUCING A HYDRODESULFURIZATION CATALYST

(71) Applicant: King Fahd University of Petroleum and Minerals, Dhahran (SA)

(72) Inventors: Khalid Alhooshani, Dhahran (SA); Saheed Adewale Ganiyu, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 147 days.

(21) Appl. No.: 15/715,688

(22) Filed: Sep. 26, 2017

(65) Prior Publication Data

US 2018/0100107 A1  Apr. 12, 2018

Related U.S. Application Data

(60) Provisional application No. 62/405,615, filed on Oct. 7, 2016.

(51) Int. Cl.
*B01J 29/03* (2006.01)
*C10G 45/06* (2006.01)
(Continued)

(52) U.S. Cl.
CPC ....... *B01J 29/0341* (2013.01); *B01J 29/0308* (2013.01); *B01J 35/002* (2013.01); *C07F 7/28* (2013.01); *C10G 45/06* (2013.01); *C10G 45/08* (2013.01); *C10G 45/12* (2013.01); *C10G 45/32* (2013.01); *C10G 65/06* (2013.01);
(Continued)

(58) Field of Classification Search
None
See application file for complete search history.

(56) References Cited

U.S. PATENT DOCUMENTS 4,595,672 A   6/1986  Ho et al.
4,652,545 A   3/1987  Lindsley et al.
(Continued)

FOREIGN PATENT DOCUMENTS

CN   106238075 A   12/2016
EP   0 721 373 A1   7/1996
EP   2 586 529 A1   5/2013

OTHER PUBLICATIONS

Huirache-Acuna, R, et al. SBA-15 Mesoporous Silica as Catalytic Support for Hydrodesulfurization Catalysts—Review, 2013, Materials, vo. 6, pp. 4139-4167. (Year: 2013).*
Olivas, A. et al., Impact of Al and Ti ions of the dispersion and performance of supported NiMo(W)/SBA-15 catalysts in the HDS and HYD reactions, 2008, Catalysis Today, vol. 143, pp. 120-125 (Year: 2008).*
(Continued)

*Primary Examiner* — Renee Robinson
*Assistant Examiner* — Derek N Mueller
(74) *Attorney, Agent, or Firm* — Oblon, McClelland, Maier & Neustadt, L.L.P.

(57) ABSTRACT

A single-pot method of producing a hydrodesulfurization catalyst by hydrothermally treating a hydrothermal precursor that includes a silica source, a structural directing surfactant, an aqueous acid solution, and metal precursors that contain active catalyst materials is provided. The hydrodesulfurization catalyst includes a catalyst support having SBA-15 and preferably titanium, wherein the active catalyst materials are homogenously deposited on the catalyst support. Various embodiments of said method and the hydrodesulfurization catalyst are also provided.

15 Claims, 31 Drawing Sheets

(51) Int. Cl.
| | | |
|---|---|---|
| *C07F 7/28* | (2006.01) | |
| *C10G 45/12* | (2006.01) | |
| *C10G 45/32* | (2006.01) | |
| *C10G 65/06* | (2006.01) | |
| *C10G 45/08* | (2006.01) | |
| *B01J 35/00* | (2006.01) | |

(52) U.S. Cl.
CPC .......... *C10G 2300/1033* (2013.01); *C10G 2300/202* (2013.01); *C10G 2300/70* (2013.01)

(56) References Cited

U.S. PATENT DOCUMENTS

| | | |
|---|---|---|
| 7,754,637 B2 | 7/2010 | Zanibelli et al. |
| 7,968,069 B2 | 6/2011 | Rayo Mayoral et al. |
| 7,981,828 B2 | 7/2011 | Devers et al. |
| 8,877,671 B2 | 11/2014 | Radlowski et al. |
| 9,278,338 B2 | 3/2016 | Coupland |
| 2014/0124410 A1 | 5/2014 | Rayo Mayoral et al. |
| 2014/0231310 A1 | 8/2014 | Marchand et al. |
| 2015/0038751 A1 | 2/2015 | Ng et al. |
| 2015/0182952 A1 | 7/2015 | Alvarez Contreras et al. |
| 2016/0136623 A1 | 5/2016 | Radlowski et al. |

OTHER PUBLICATIONS

Haukka, S., Adsoprtion Controlled Preparation of Heterogeneous Catalysts, Studies in Surface Science and Catalysis, 2003, vol. 120, pp. 715-750. (Year: 2003).*
Nava, R., et al., CoMo/Ti-SBA-15 Catalysts for Dibenzothiopene Desulfurization, 2007, Catal. Today, vol. 127, pp. 70-84. (Year: 2007).*
Sigma-Adrich catalog entry for Pluronic P123 (Year: 2019).*
Gutierrez, et al., SBA-15 supports modified by Ti and Zr grafting for NiMo hydrodesulfurization catalysts, 2006, Catal. Today, vol. 116, pp. 485-497 (Year: 2006).*
Park, et al., Single-step preparation of Ni catalysts supported on mesoporous silicas (SBA-15 and SBA-16) and the effect of pore structure on the selective hydrodechlorination of 1,1,2-trichloroethane to VCM, 2004, Catal. Today, vol. 97, pp. 195-203 (Year: 2004).*
Wei, Q. et al., "TiO2—SiO2-Composite-Supported Catalysts for Residue Fluid Catalytic Cracking Diesel Hydrotreating", Energy & Fuels, vol. 28, pp. 7343-7351, (Oct. 27, 2014).
Mendoza-Nieto, J.A., et al., "Effect of Titania Grafting on Behavior of NiMo Hydrodesulfurization Catalysts Supported on Different Types of Silica", Fuel, vol. 100, pp. 100-109, (Feb. 24, 2012).

* cited by examiner

METHOD FOR PRODUCING A HYDRODESULFURIZATION CATALYST

CROSS REFERENCE TO RELATED APPLICATIONS

This application is based on, and claims the benefit of priority to, provisional application No. 62/405,615 filed Oct. 7, 2016, the entire contents of which are incorporated herein by reference.

STATEMENT OF FUNDING ACKNOWLEDGEMENT

The authors acknowledge the support provided by King Fahd University of Petroleum & Minerals (KFUPM) for funding through project no. DSR NUS15105.

BACKGROUND OF THE INVENTION

Technical Field

The present invention relates to a hydrodesulfurization catalyst, and a single-pot method of producing the hydrodesulfurization catalyst.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Stringent environmental regulations limit the sulfur content allowed in transportation fuels and sulfur-free fuel cells continue to be a challenge. Research efforts are therefore aimed at improving the activity and the stability of hydrodesulfurization (HDS) catalysis. These improvements are generally obtained by changing or modifying the type or nature of the catalyst support, the active metals, the synthesis routes, and the use of organic or inorganic additives in the catalyst [C. Song, An overview of new approaches to deep desulfurization for ultra-clean gasoline, diesel fuel and jet fuel, Catalysis today, 86 (2003) 211-263; C. Song, Fuel processing for low-temperature and high-temperature fuel cells: Challenges, and opportunities for sustainable development in the 21st century, Catalysis today, 77 (2002) 17-49].

$\gamma$-$Al_2O_3$ has been widely used as a catalyst support for hydrotreating catalysts, but it strongly interacts with the active phase metal ($MoO_3$) in a mono-layered tetrahedral coordination. This interaction inhibits active phase reduction, which in turn decreases catalytic activity compared to octahedral Mo [L. Qu, W. Zhang, P. J. Kooyman, R. Prins, MAS NMR, TPR, and TEM studies of the interaction of NiMo with alumina and silica-alumina supports, Journal of Catalysis 215 (2003) 7-13]. Mesoporous supports, such as silica, zeolite, carbon, titania, and mixed metal oxides, are shown to provide improved catalytic activities to the catalyst compared to $\gamma$-$Al_2O_3$ catalyst supports [V. Sundaramurthy, I. Eswaramoorthi, A. K. Dalai, J. Adjaye, Hydrotreating of gas oil on SBA-15 supported NiMo catalysts, Microporous and Mesoporous Materials 111 (2008) 560-568; T. Klimova, L. Pena, L. Lizama, C. Salcedo, O. Y. Gutidrrez, Modification of activity and selectivity of NiMo/SBA-15 HDS catalysts by grafting of different metal oxides on the support surface, Industrial & Engineering Chemistry Research 48 (2008) 1126-1133; J. C. Duchet, M. J. Tilliette, D. Cornet, L. Vivier, G. Perot, L. Bekakra, C. Moreau, G. Szabo, Catalytic properties of nickel molybdenum sulfide supported on zirconia, Catalysis today 10 (1991) 579-592; and G. M. Kumaran, S. Garg, K. Soni, V. Prasad, L. D. Sharma, G. M. Dhar, Catalytic functionalities of H-$\beta$-zeolite-supported molybdenum hydrotreating catalysts, Energy & fuels 20 (2006) 1784-1790; and M. Breysse, P. Afanasiev, C. Geantet, M. Vrinat, Overview of support effects in hydrotreating catalysts, Catalysis Today 86 (2003) 5-16; and N. Prabhu, A. K. Dalai, J. Adjaye, Hydrodesulfurization and hydrodenitrogenation of light gas oil using NiMo catalyst supported on functionalized mesoporous carbon, Applied Catalysis A: General 401 (2011) 1-11].

SBA-15 is one of the most studied mesoporous silica materials due to its high surface-to-volume ratio, high pore size, highly ordered 2D hexagonal structure, good mechanical strength, and thick pore wall, which is responsible for hydrothermal stability. SBA-15 possesses a combination of micropores (~0.5 to 3.0 nm) and mesopores (~4 to 14 nm) in a uniform hexagonal tunable pore structure [V. Meynen, P. Cool, E. Vansant, Synthesis of siliceous materials with micro- and mesoporosity, Microporous and mesoporous materials, 104 (2007) 26-38]. Recently, the use of SBA-15 as an HIDS support has increased because of the good catalytic properties. However, poor dispersion of the active phase(s) and hydrothermal stability resulting from the amorphous silica wall have hindered its full catalytic potential.

Different modification approaches have been reported to overcome the limitations associated with the SBA-15, such as incorporation of transition metals, chelating agents, and/or additives to SBA-based HDS catalysts. For example, nitriloacetic acid (NTA), ethylenediaminetetraacetic acid (EDTA), cyclohexanediaminetetraacetic acid (CyDTA), and citric acid (CA) as different chelating agents, have been shown to improve the performance of SBA-based HDS catalysts [S. Badoga, K. C. Mouli, K. K. Soni, A. Dalai, J. Adjaye, Beneficial influence of EDTA on the structure and catalytic properties of sulfided NiMo/SBA-15 catalysts for hydrotreating of light gas oil, Applied catalysis. B, Environmental, 125 (2012) 67-84; and N. Rinaldi, T. Kubota, Y. Okamoto, Effect of Citric Acid Addition on Co—$MoB_2O_3$/$Al_2O_3$ Catalysts Prepared by a Post-Treatment Method, Industrial & engineering chemistry research, 48 (2009) 10414-10424; and G. Kishan, L. Coulier, V. De Beer, J. Van Veen, J. Niemantsverdriet, Sulfidation and thiophene hydrodesulfurization activity of nickel tungsten sulfide model catalysts, prepared without and with chelating agents, Journal of catalysis, 196 (2000) 180-189; and M. S. Rana, J. Ramirez, A. Gutierrez-Alejandre, J. Ancheyta, L. Cedeño, S. Maity, Support effects in CoMo hydrodesulfurization catalysts prepared with EDTA as a chelating agent, Journal of catalysis, 246 (2007) 100-108]. Also, addition of chelating agents renders $\beta$-$CoMoO_4$ or $NiMoO_4$ soluble by increasing the dispersion of Co or Mo without blocking active sites [M. Lélias, E. Le Guludec, L. Maricy, J. Van Gestel, A. Travert, L. Oliviero, F. Maugé, Effect of EDTA addition on the structure and activity of the active phase of cobalt-molybdenum sulfide hydrotreatment catalysts, Catalysis Today, 150 (2010) 179-185]. The incorporation of heteroatoms (Ti, Zr, and Al) and organic functional groups, either directly or via a post-synthesis approach, have shown to improve the stability and the activity of SBA-based HDS catalysts [R. Huirache-Acuña, R. Nava, C. L. Peza-Ledesma, J. Lara-Romero, G. Alonso-Nuez, B. Pawelec, E. M. Rivera-Mufloz, SBA-15 Mesoporous Silica as Catalytic Support for Hydrodesulfurization Catalysts—Review, Materials, 6 (2013) 4139-4167]. The heteroatoms are Lewis acids that can improve the dispersion of the active phase by increasing the metal-support interactions (MSI) from low to moderate. Sandeep, et al. (2014) studied the combined effect of heteroatoms and complexing agents in the direct synthesis of M-SBA-15 (M=Ti, Zr, and Al) followed by dispersion of the active phase with the aid of EDTA via the impregnation method. The HDS activities for NiMo/Ti-SBA-15 and NiMo/Ti-SBA-15/2 EDTA were improved by 12% and 18%, respectively, as a result of the increased surface acidity and metal-support interactions [S. Badoga, A. K. Dalai, J. Adjaye, Y. Hu, Combined Effects of EDTA and Heteroatoms (Ti, Zr, and Al) on Catalytic Activity of SBA-15 Supported NiMo Catalyst for Hydrotreating of Heavy Gas Oil, Industrial & engineering chemistry research, 53 (2014) 2137-2156].

Lara, et al. (2014) reported the significance of EDTA and CA towards enhancing the HDS catalytic activity (91.6% after 8 hours of reaction) of dibenzothiophene (DBT). They claimed that the use of chelating agents avoided the formation of a crystalline ($CoMoO_4$) phase and resulted in a better dispersion of $MoO_3$, as confirmed by X-ray powder diffraction (XRD) and high-resolution transmission electron microscopy (HRTEM) [L. Pena, D. Valencia, T. Klimova, CoMo/SBA-15 catalysts prepared with EDTA and citric acid and their performance in hydrodesulfurization of dibenzothiophene, Applied Catalysis B: Environmental, 147 (2014) 879-887]. Miguel, et al. (2014) studied the amount of CA required to achieve a higher activity and selectivity of NiMo/SBA-15 in deep HDS. Their results showed that the addition of CA at a ratio of 1:1 (CA:Mo) resulted in an increase in the degree of sulfidation and thus a good dispersion of the catalytically active phase ($MoS_2$), which significantly improved the hydrodesulfurization of DBT and 4,6-dimethyldibenzothiophene (DMDBT) [L. Pena, D. Valencia, T. Klimova, CoMo/SBA-15 catalysts prepared with EDTA and citric acid and their performance in hydrodesulfurization of dibenzothiophene, Applied Catalysis B: Environmental, 147 (2014) 879-887]. By establishing the correlation between the concentration of Mo and Ni on the edges of sulfide particles and the catalytic HDS activities, Oliver, et al. (2014) highlighted the influence of the nature of the support on the dispersion of non-promoted catalysts and the degree of Ni decoration on the edges of the Ni—Mo—S phase [O. Y. Gutierrez, S. Singh, E. Schachtl, J. Kim, E. Kondratieva, J. Hein, J. A. Lercher, Effects of the Support on the Performance and Promotion of (Ni) $MoS_2$ Catalysts for Simultaneous Hydrodenitrogenation and Hydrodesulfurization, ACS Catalysis, 4 (2014) 1487-1499].

The performance of HDS catalysts having additives such as fluorine and phosphorous have been reported, but non-noble metal-based HDS catalysts, such as transition metal phosphides with SBA-15 and molybdenum carbide-SBA-15, have not been extensively studied, despite their excellent HDS activities [Z. Liu, L. Zhang, J. Jiang, C. Bian, Z. Zhang, Z. Gao, Advancement of hydro-desulfurization catalyst and discussion of its application in coal tar, (2013); and P. Y. Wu, S. F. Ji, L. H. Hlu, J. Q. Zhu, C. Y. Li, Preparation, characterization, and catalytic properties of the $Mo_2C$/SBA-15 catalysts, Journal of Porous Materials, 15 (2008) 181-187]. However, supported noble metals are susceptible to sulfur poisoning, due to the strong interactions of said noble metals with $H_2S$, which limits their use in hydrotreating processes [P. Castaflo, B. Pawelec, J. Fierro, J. Arandes, J. Bilbao, Enhancement of pyrolysis gasoline hydrogenation over Pd-promoted Ni/$SiO_2$—$Al_2O_3$ catalysts, Fuel, 86 (2007) 2262-2274]. The synthesis routes and conditions of the support, which can improve textural properties, provide alternative ways to improve the catalytic activity of HDS catalysts.

Despite extensive research efforts to improve the catalytic activities of SBA-15, including the deposition of active metals via equilibrium adsorption, sequential and co-impregnation, mechanical mixing, sol-gel approaches, and grafting; there appears to be no literature report on a "single-pot" synthesis of SBA-15-Me or Ti-SBA-15-Me (Me=active catalyst material) with or without a complexing agent to produce HDS catalysts.

In view of the forgoing, one objective of the present invention is to provide a "single-pot" method of producing a hydrodesulfurization catalyst (HDS catalyst) by hydrothermally treating a hydrothermal precursor that includes a silica source, a structural directing surfactant, an aqueous acid solution, and metal precursors that contain active catalyst materials. The resulting HDS catalyst includes a catalyst support having SBA-15 and preferably titanium, wherein the active catalyst materials are homogenously deposited on the catalyst support.

BRIEF SUMMARY OF THE INVENTION

According to a first aspect, the present disclosure relates to a method of producing a hydrodesulfurization catalyst, involving hydrothermally treating a hydrothermal precursor including a silica source, a structural directing surfactant, an aqueous acid solution, a first metal precursor, and a second metal precursor, to form the hydrodesulfurization catalyst, wherein each of the first and the second metal precursors includes an active catalyst material selected from groups 4 to 12 of the periodic table, and wherein the hydrodesulfurization catalyst includes at least two active catalyst materials deposited on a catalyst support comprising SBA-15.

In one embodiment, the method further involves calcining the hydrodesulfurization catalyst at a temperature in the range of 200 to 650° C.

In one embodiment, the hydrodesulfurization catalyst is calcined at a temperature in the range of 250 to 350° C. for 2 to 12 hours.

In one embodiment, the hydrothermal precursor further includes a titanium source, and the catalyst support further includes titanium.

In one embodiment, the hydrothermal precursor does not include a complexing agent.

In one embodiment, the hydrothermal precursor further includes a complexing agent comprising citric acid.

In one embodiment, the first metal precursor includes an active catalyst material selected from nickel and cobalt, and the second metal precursor includes an active catalyst material selected from molybdenum and tungsten.

In one embodiment, the first metal precursor is nickel nitrate and the second metal precursor is ammonium molybdate.

In one embodiment, a weight ratio of molybdenum to nickel in the hydrothermal precursor is in the range of 2:1 to 8:1.

In one embodiment, the hydrothermal precursor is formed by i) mixing the structural directing surfactant with the aqueous acid solution to form an acid-surfactant solution and stirring the acid-surfactant solution for at least 30 minutes, ii) mixing the acid-surfactant solution with the silica source to form a catalyst support mixture and stirring the catalyst support mixture for at least 20 hours, iii) mixing the catalyst support mixture with the first and the second metal precursors.

In one embodiment, the hydrothermal precursor further includes a titanium source, and the method further involves mixing the titanium source with the catalyst support mixture prior to mixing the catalyst support mixture with the first and the second metal precursors.

In one embodiment, a molar ratio of silicon in the silica source to the titanium in the titanium source is in the range of 5:1 to 20:1.

In one embodiment, the silica source is a tetraalkyl orthosilicate, and the titanium source is a titanium alkoxide.

In one embodiment, the silica source is tetraethyl orthosilicate, and the titanium source is titanium isopropoxide.

In one embodiment, the structural directing surfactant is a triblock copolymer comprising poly(ethylene oxide) and poly(propylene oxide).

According to a second aspect, the present disclosure relates to a hydrodesulfurization catalyst, including i) a catalyst support that includes SBA-15 and titanium, wherein a molar ratio of silicon in the SBA-15 to titanium is in a range of 5:1 to 20:1, ii) at least two active catalyst materials selected from the group consisting of nickel, molybdenum, cobalt, and tungsten, wherein said at least two active catalyst materials are homogenously deposited on the catalyst support, and wherein the hydrodesulfurization catalyst has a BET surface area of at least 300 m$^2$/g, and a surface acidity of at least 0.19 mmol/g.

In one embodiment, the hydrodesulfurization catalyst has a total pore volume in the range of 0.4 to 1.0 cm$^3$/g, and an average pore size in the range of 5 to 8 nm.

According to a third aspect, the present disclosure relates to a method of hydro-desulfurizing a hydrocarbon feedstock, involving contacting the hydrocarbon feedstock including at least one sulfur-containing hydrocarbon compound with the hydrodesulfurization catalyst in the presence of hydrogen gas to hydro-desulfurize the at least one sulfur-containing hydrocarbon compound to form hydrogen sulfide and a hydro-desulfurized hydrocarbon compound, wherein the hydrocarbon feedstock is contacted with the hydrodesulfurization catalyst at a temperature in the range of 200 to 500° C., and wherein a pressure of the hydrogen gas is in the range of 2 to 10 MPa.

In one embodiment, the method of hydro-desulfurizing the hydrocarbon feedstock further involves i) treating the hydrodesulfurization catalyst with a gaseous mixture comprising hydrogen gas at a temperature in the range of 300 to 500° C. to reduce at least a portion of active catalyst materials present in the hydrodesulfurization catalyst, ii) presulfiding the hydrodesulfurization catalyst with a sulfide-containing solution at a temperature in the range of 250 to 450° C., prior to the contacting.

In one embodiment, the hydrocarbon feedstock is contacted with the hydrodesulfurization catalyst for no more than 6 hours, wherein a ratio of a concentration of the sulfur-containing hydrocarbon compound in the hydrocarbon feedstock after the contacting to the concentration of the sulfur-containing hydrocarbon compound in the hydrocarbon feedstock before the contacting is in the range of 1:10 to 1:1,000.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
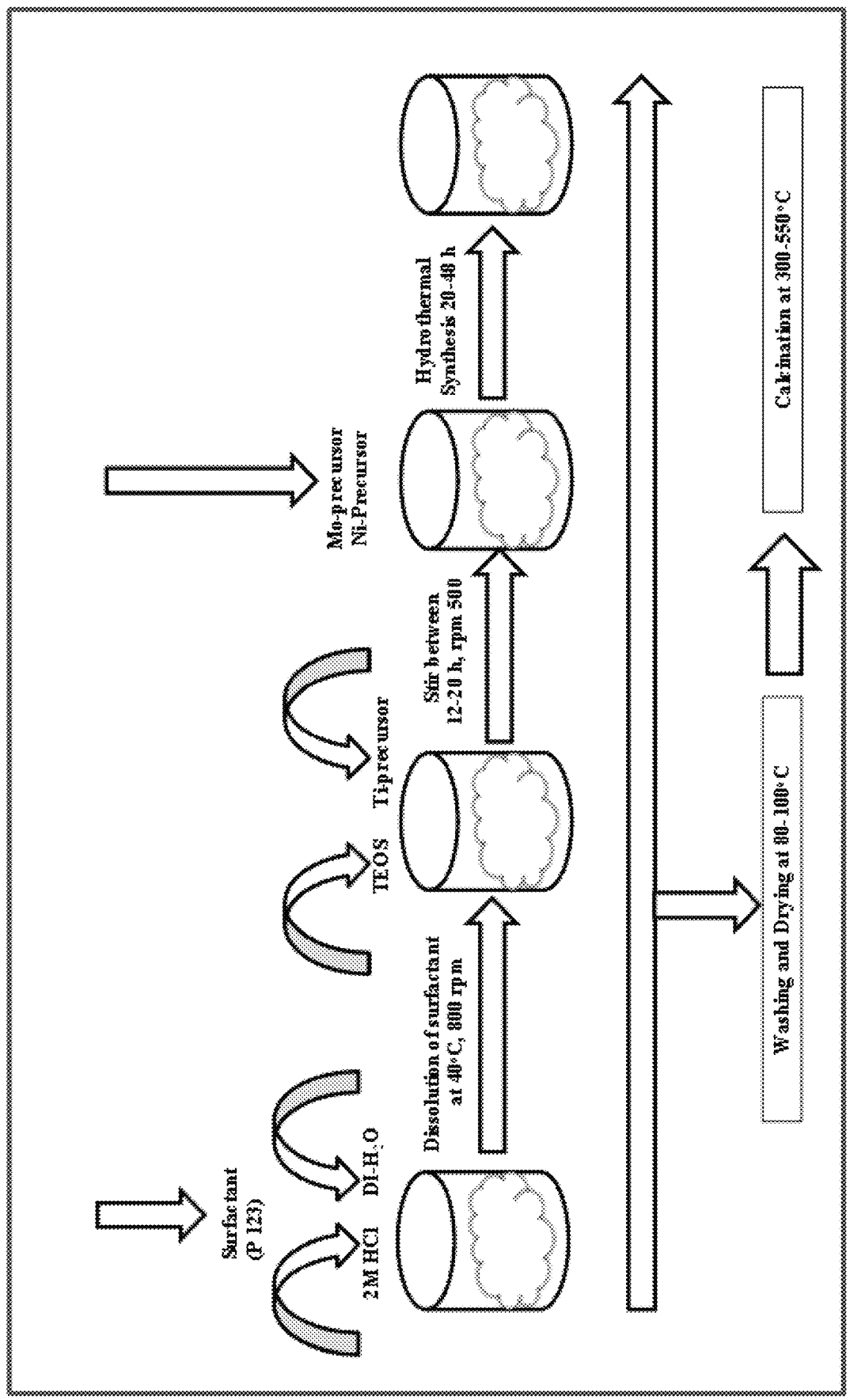
FIG. 1 is a schematic that represents processing steps of producing a hydrodesulfurization (HDS) catalyst via a "single-pot" method.

According to a first aspect, the present disclosure relates to a method of producing a hydrodesulfurization (HDS) catalyst, which is also referred to as a "single-pot" synthesis method in this disclosure. The single-pot method involves hydrothermally treating a hydrothermal precursor that includes a silica source, a structural directing surfactant, an aqueous acid solution, a first metal precursor, and a second metal precursor.

The term "single-pot" as used in this disclosure refers to a processing approach whereby raw materials of the HDS catalyst, i.e. the silica source, the structural directing surfactant, the aqueous acid solution, the first metal precursor, and the second metal precursor, are successively subjected to physical and/or chemical processes and reactions in a single pot (e.g., a single reactor or single vessel). The single-pot method may eliminate separation and purification processes of intermediate compounds, and thus may reduce the synthesis cost, reduce the time of operation, and improve product yield.

Accordingly, in a preferred embodiment, the structural directing surfactant is first mixed with the aqueous acid solution to form an acid-surfactant solution. A weight ratio of the aqueous acid solution to the structural directing surfactant may vary depending on the type of acid and the structural directing surfactant and a concentration of the aqueous acid solution. For example, in some embodiments, the aqueous acid solution is an aqueous hydrochloric acid solution with a concentration of hydrochloric acid in the range of 1.0 to 5.0 M, preferably 1.5 to 3.0, more preferably about 2.0 M, and the structural directing surfactant is a triblock copolymer of poly(ethylene oxide) (PEO) and poly(propylene oxide) (PPO) with a repeating unit of PEO-PPO-PEO. Accordingly, a weight ratio of the aqueous acid solution to the structural directing surfactant is in the range of from about 50:1 to about 10:1, preferably from about 40:1 to about 20:1, preferably from about 35:1 to about 25:1, more preferably about 30:1. In a preferred embodiment, water, e.g. deionized water, is mixed with the acid-surfactant solution. Preferably, said water has a high purity with a conductivity in the range 5 to 100 µS/cm (microsiemens per centimeter), preferably 10 to 50 µS/cm, preferably 12 to 40 µS/cm, preferably 15 to 30 µS/cm, preferably about 18 µS/cm. A pH of the acid-surfactant solution may vary depending on an amount of water and the concentration of the aqueous acid solution. Preferably, the pH of the acid-surfactant solution is in the range of 1 to 7, preferably 1 to 6, preferably 1 to 5, preferably 1 to 2.

Alternative aqueous acid solutions that may be utilized in the method of producing the HDS catalyst includes, but are not limited to, sulfuric acid ($H_2SO_4$), perchloric acid ($HClO_4$), hypochlorous acid (HClO), chlorous acid ($HClO_2$), chloric acid ($HClO_3$), nitrous acid ($HNO_2$), nitric acid ($HNO_3$), carbonic acid ($H_2CO_3$), oxalic acid ($H_2C_2O_4$), acetic acid ($CH_3COOH$), and phosphoric acid ($H_3PO_4$).

In one embodiment, the structural directing surfactant is a poly-ethylene glycol-containing diblock copolymer such as a PEG-PLA (poly-lactic acid) diblock copolymer, e.g. poly(ethylene glycol) methyl ether-block-poly(D,L lactide), a PEG-PLGA (poly lactic glycol acid) diblock copolymer, e.g. poly(ethylene glycol) methyl ether-block-poly(L-lactide-co-glycolide), a PEG-PCL (polycaprolactone) diblock copolymer, e.g. poly(ethylene oxide)-block-polycaprolactone, a PEG-PE (polyethylene) diblock copolymer, e.g. polyethylene-block-poly(ethylene glycol), or a PEG-PS (polystyrene) diblock compolymer, e.g. poly(styrene)-block-poly(ethylene glycol). In another embodiment, the structural directing surfactant is a polystyrene-containing diblock copolymer such as poly(styrene-block-methyl methacrylate), polystyrene-block-poly(acrylic acid), or polystyrene-block-poly(tert-butyl acrylate). In an alternative embodiment, the structural directing surfactant is a polystyrene-containing triblock copolymer such as polystyrene-block-polybutadiene-block-polystyrene, polystyrene-block-poly(ethylene)-block-polystyrene, polystyrene-block-poly(butylene)-block-polystyrene, or polystyrene-block-polyisoprene-block-polystyrene. However, in a preferred embodiment, the structural directing surfactant is a triblock copolymer of PEG-PPG-PEG, or PPG-PEG-PPG, wherein PPG is polypropylene glycol and PEG is polyethylene glycol. In another preferred embodiment, the structural directing surfactant is a triblock copolymer of PEO-PPO-PEO or PPO-PEO-PPO, wherein PEO is poly(ethylene oxide) and PPO is poly(propylene oxide). In the most preferred embodiment, the triblock copolymer is $PEO_x$—$PPO_y$—$PEO_z$, wherein x, y, and z are repeating units of PEO, PPO, and PEO, respectively, and x has a value in the range of 5 to 50, preferably 10 to 40, preferably about 20; y has a value in the range of 50 to 100, preferably 60 to 80, preferably about 70; and z has a value in the range of 5 to 50, preferably 10 to 40, preferably about 20. A molecular weight of the structural directing surfactant that is used in this disclosure may vary from about 1,000 to about 20,000 g/mol, preferably from about 2,000 to about 10,000 g/mol, preferably from about 3,000 to about 8,000 g/mol, preferably from about 4,000 to about 7,000 g/mol.

Preferably, the acid-surfactant solution is stirred for at least 30 minutes, preferably at least 40 minutes, preferably at least 50 minutes, but no more than 1 hour, at a temperature in the range of 20 to 60° C., preferably 30 to 50° C., preferably 35 to 45° C., preferably about 40° C., with a stirring speed of 300 to 800 rpm, preferably 400 to 600 rpm, preferably about 500 rpm. Then, the acid-surfactant solution is mixed with the silica source to form a catalyst support mixture. Preferably, a weight ratio of the silica source to the structural directing surfactant in the acid-surfactant solution is in the range of 1:1 to 5:1, preferably 1.5:1 to 3:1, preferably 2:1 to 2.5:1.

In one embodiment, the silica source is silica particles and/or silica nanoparticles ($SiO_2$). However, in some preferred embodiments, the silica source is a tetraalkyl orthosilicate. Exemplary tetraalkyl orthosilicates include, but are not limited to tetraethyl orthosilicate, tetramethyl orthosilicate, tetrapropyl orthosilicate, and tetrabutyl orthosilicate. In the most preferred embodiment, the silica source is tetraethyl orthosilicate. In addition, polydimethylsiloxane (PDMS), sodium silicate, tetramethylammonium silicate, and/or sodium metasilicate may also be used in combination with the silica source.

The resulting mixture after mixing the acid-surfactant solution with the silica source, i.e. the catalyst support mixture, is stirred at a temperature in the range of 20 to 60° C., preferably 30 to 50° C., preferably 35 to 45° C., preferably about 40° C., and a stirring speed of 300 to 800 rpm, preferably 400 to 600 rpm, preferably about 500 rpm, for at least 4 hours, preferably at least 8 hours, preferably at least 12 hours, preferably at least 16 hours, preferably at least 20 hours, preferably at least 22 hours, but no more than 24 hours.

After that, the catalyst support mixture is mixed with the first and the second metal precursors and stirred for at least 1 hour, preferably at least 2 hours, preferably at least 3 hours, but no more than 6 hours at a temperature in the range of 20 to 40° C., preferably 22 to 30° C., preferably about 25° C., to form the hydrothermal precursor. The term "metal precursor" as used in this disclosure refers to a pre-made solution that contains one or more active catalyst materials selected from groups 4 to 12 of the periodic table in cationic form or elemental form. Exemplary active catalyst materials include molybdenum, tungsten, nickel, cobalt, manganese, iron, copper, zinc, zirconium, niobium, ruthenium, rhodium, palladium, silver, gold, platinum, iridium, osmium, tantalum, and hafnium. In some preferred embodiments, the active catalyst materials are selected from groups 6, 9 and 10 of the periodic table. Preferably, the first and second metal precursors are different, i.e. they contain a different metal. For example, in some embodiments the first metal precursor contains an active catalyst material selected from nickel and cobalt, and the second metal precursor contains an active catalyst material selected from molybdenum, cobalt, and tungsten. Preferably, the first metal precursor is nickel nitrate and hydrates thereof, and the second metal precursor is ammonium molybdate. In some preferred embodiments, the first metal precursor contains nickel, and the second metal precursor contains molybdenum, wherein a weight ratio of molybdenum to nickel in the hydrothermal precursor is in the range of 2:1 to 8:1, preferably 3:1 to 7:1, preferably 3.5:1 to 6:1, preferably 4:1 to 5:1, preferably about 4.3:1.

In one embodiment, the first and the second metal precursors are mixed together and stirred for at least 10 minutes, preferably at least 20 minutes, preferably at least 30 minutes, but no more than 2 hours, preferably no more than 1 hour, at a temperature in the range of 20 to 40° C., preferably 22 to 30° C., preferably about 25° C., prior to mixing with the catalyst support mixture. In another embodiment, the first metal precursor is mixed with the catalyst support mixture and stirred for at least 10 minutes, preferably at least 20 minutes, preferably at least 30 minutes, but no more than 2 hours, preferably no more than 1 hour, prior to mixing the second metal precursor thereto. Alternatively, in another embodiment, the second metal precursor is mixed with the catalyst support mixture and stirred for at least 10 minutes, preferably at least 20 minutes, preferably at least 30 minutes, but no more than 2 hours, preferably no more than 1 hour, prior to mixing the first metal precursor thereto. Preferably, a temperature of the catalyst support mixture remains substantially unchanged, i.e. in the range of 20 to 40° C., preferably 22 to 30° C., preferably about 25° C. Each of the first and the second precursors may be mixed with the catalyst support mixture in a dropwise manner with a mixing rate of no more than 0.5 L/min, preferably no more than 1.0 L/min. Alternatively, the first and the second precursors may be mixed with the catalyst support mixture at a mixing rate of at least 10 mL/s, preferably at least 20 mL/s, preferably at least 50 mL/s, preferably at least 100 mL/s, preferably at least 500 mL/s, preferably at least 1.0 L/s, but no more than 2.0 Us. In some embodiments, a complexing agent and/or a surfactant may be mixed with the catalyst support mixture along with mixing the first and the second metal precursors.

The hydrothermal precursor is placed into a stainless steel container, i.e. an autoclave, which can bear a temperature of up to 300° C., preferably up to 400° C., and a pressure of up to 20 bars, preferably up to 30 bars, more preferably up to 50 bars. The stainless steel container may contain a Teflon® liner, and scaling of the stainless steel container may preferably be provided by metal end caps and temperature resistant rubber gaskets. The autoclave may preferably be equipped with a safety valve to control an internal pressure of the autoclave. Accordingly, the hydrothermal precursor is hydrothermally treated in the autoclave for 5 to 50 hours, preferably 10 to 40 hours, preferably 20 to 30 hours, preferably 22 to 28 hours, preferably about 24 hours, in a temperature in the range of 80 to 250° C., preferably 90 to 150° C., preferably 95 to 120° C., preferably about 100° C., and under a pressure in the range of 1.5 to 10 bars, preferably 2 to 8 bars, preferably 3 to 6 bars. During the hydrothermal treatment, silica crystals may encapsulate the structural directing surfactants, i.e. self-assembled block copolymers, and thus crystallites with a hexagonal array of pores, i.e. SBA-15, may form in the hydrothermal precursor. The active catalyst materials, e.g. molybdenum, tungsten, nickel, cobalt, etc. may be deposited on at least a portion of the SBA-15, thus forming the HDS catalyst that includes at least two active catalyst materials deposited on a catalyst support, i.e. SBA-15.

In a preferred embodiment, the at least two active catalyst materials are deposited on at least a portion of an external surface area of the catalyst support, when the HDS catalyst is produced via the single-pot method. Accordingly, said active catalyst materials are deposited on at least 50%, preferably at least 60%, preferably at least 70%, preferably at least 80%, preferably at least 90%, preferably at least 95%, preferably at least 99%, of the external surface area of the catalyst support, i.e. SBA-15. Preferably, a thickness of the active catalyst materials that are deposited on at least a portion of the external surface area of the catalyst support may be no more than 500 nm, preferably no more than 200 nm, preferably no more than 100 nm, preferably no more than 50 nm, preferably no more than 20 nm, preferably no more than 10 nm.

In a preferred embodiment, the at least two active catalyst materials are homogenously deposited on the catalyst support, when the HDS catalyst is produced via the single-pot method. The term "homogenously deposited" as used in this disclosure refers to a condition wherein a surface density of the active catalyst materials in any surface sub-section of the HDS catalyst with an area of one square micron, is at least 10 ng, preferably at least 100 ng, preferably at least 1.0 μg, preferably at least 5.0 μg, but no more than 10.0 μg. Alternatively, the term "homogenously deposited" as used herein may be defined as a condition wherein a surface density of the active catalyst materials in any surface sub-section of the HDS catalyst differs by no more than 10%, preferably by no more than 5% from the surface density of the active catalyst materials in another surface sub-section with substantially the same surface area.

Figure 16:
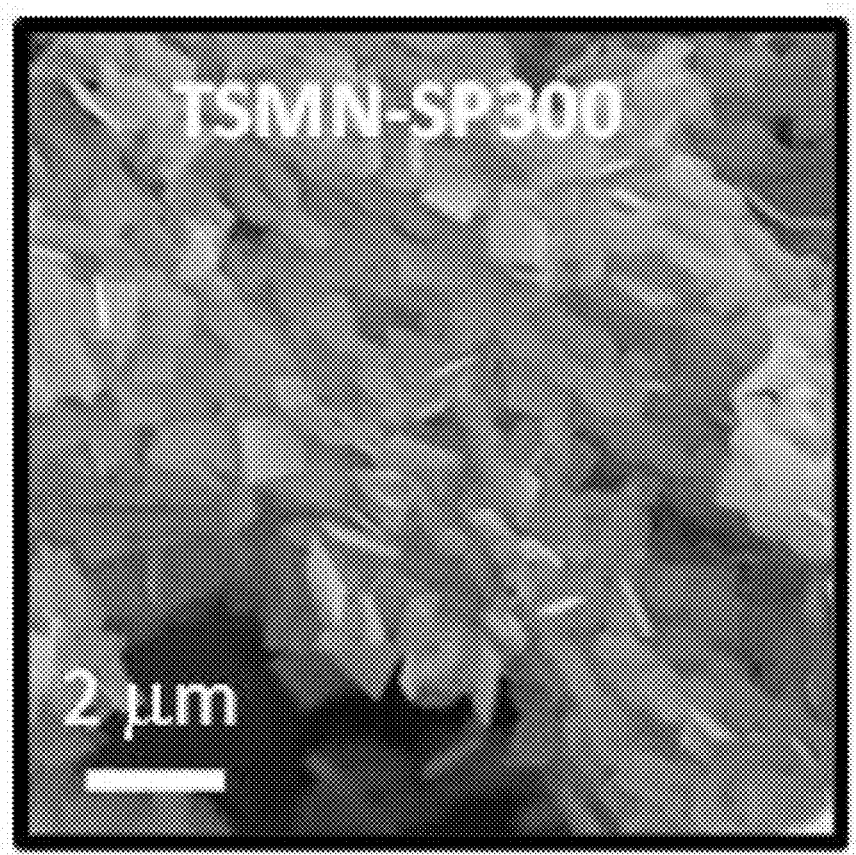
FIG. 16 is a SEM micrograph of the HDS catalyst that is produced via the single-pot method and calcined at 300° C.
Figure 17:
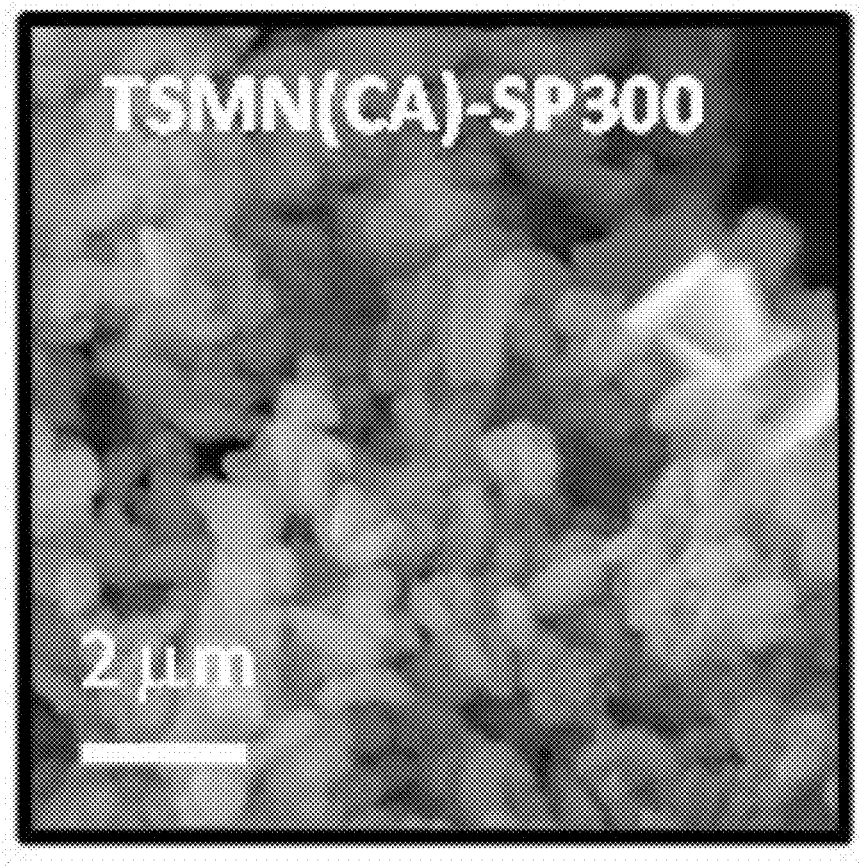
FIG. 17 is a SEM micrograph of the HDS catalyst that is produced via the single-pot method in the presence of a complexing agent, calcined at 300° C.

Morphology of the HDS catalyst that is produced via the single-pot method without the presence of a complexing agent is shown in SEM micrographs of FIG. 16, and the morphology of the HDS catalyst that is produced via the single-pot method with the presence of a complexing agent is shown in SEM micrographs of FIG. 17. Also, the morphology of the HDS catalyst that is produced via an impregnation method without the presence of a complexing agent is shown in SEM micrographs of FIG. 18, and the morphology of the HDS catalyst that is produced via an impregnation method with the presence of a complexing agent is shown in SEM micrographs of FIG. 19. Accordingly, a nano-cubical flat-sheet morphology of the active catalyst materials is observed in the HDS catalyst that is produced via the single-pot method, and the nano-cubical flat-sheet morphology is grown alongside the rod-like morphology of the catalyst support, i.e. titanium-modified SBA-15. However, little or no active catalyst materials are observed on the catalyst support of the HDS catalyst that is produced via the impregnation method.

In some embodiments, when the hydrothermal precursor is hydrothermally treated, the HDS catalyst is taken out from the autoclave. Accordingly, the autoclave is first taken out from the heating condition and cooled down to room temperature, i.e. a temperature in the range of 20 to 40° C., preferably 22 to 30° C., preferably about 25° C., for example by sinking the autoclave in water. After a temperature of the autoclave is lowered to approximately room temperature, the safety valve is loosened to leak internal pressure. Once an internal pressure of the autoclave reaches the atmospheric pressure, i.e. a pressure of about 1 atm, the HDS catalyst is taken out of the autoclave. In a preferred embodiment, the HDS catalyst and the hydrothermal precursor are centrifuged with a rotational speed of no more than 3,000 rpm, preferably in the range of 1,600 to 2,500 rpm to separate the HDS catalyst from the hydrothermal precursor. The HDS catalyst may further be washed with deionized water and one or more organic solvents e.g. acetone, methanol, toluene, benzene, xylene, etc. In one embodiment, the HDS catalyst is thermally dried at a temperature in the range of 80 to 150° C., preferably 90 to 120° C., preferably about 100° C., for at least 8 hours, preferably at least 12 hours, but no more than 15 hours.

Although the HDS catalyst may be utilized directly in a hydrodesulfurization process, the HDS catalyst may optionally be calcined at a temperature in the range of 200 to 650° C., preferably 250 to 550° C., preferably 275 to 450° C., more preferably 290 to 350° C., most preferably 300 to 325° C. In the most preferred embodiment, the HDS catalyst contains nickel and molybdenum and the HDS catalyst is calcined at a temperature in the range of 250 to 350° C., preferably 290 to 325° C., preferably about 300° C., for 2 to 12 hours, preferably 4 to 10 hours, preferably about 6 hours. Calcining the HDS catalyst that contains nickel and molybdenum at a temperature above 350° C. is not preferred, since a portion of nickel and molybdenum may form $NiMoO_4$ crystals, and may affect a BET surface area, a total pore volume per unit mass of the HDS catalyst, and a surface acidity of the HDS catalyst. In view of that, the BET surface area of the HDS catalyst that is calcined at a temperature in the range of 250 to 350° C., preferably 290 to 325° C., preferably about 300° C., is about 30% to about 60%, preferably about 40% to about 55% higher than the BET surface area of substantially the same HDS catalyst that is calcined at a temperature in the range of 500 to 650° C., or 550 to 600° C. Furthermore, the total pore volume per unit mass of the HDS catalyst that is calcined at a temperature in the range of 250 to 350° C., preferably 290 to 325° C., preferably about 300° C., is 20% to 70%, preferably 30% to 60% higher than the total pore volume per unit mass of substantially the same HDS catalyst that is calcined at a temperature in the range of 500 to 650° C., or 550 to 600° C. Also, the surface acidity of the HDS catalyst that is calcined at a temperature in the range of 250 to 350° C., preferably 290 to 325° C., preferably about 300° C., is 10% to 40%, preferably 20% to 30% higher than the surface acidity of substantially the same HDS catalyst that is calcined at a temperature in the range of 500 to 650° C., or 550 to 600° C. FIG. 1 schematically represents processing steps of the method of producing the HDS catalyst.

According to the single-pot method, as described in the first aspect, the active catalyst materials are imbedded or incorporated into the catalyst support without having a post-processing step to incorporate the active catalyst materials into the catalyst support. The post processing steps that are eliminated in the single-pot method may include incipient wetness impregnation, co-impregnation, sol-gel impregnation, ion exchange, etc. The single-pot method differs from conventional impregnation or sol-gel methods, wherein the catalyst support is formed and then the active catalyst material is incorporated via one or more post-processing steps. In view of that, the single-pot method may eliminate separation, purification, washing, centrifugation, etc. steps to recover intermediate compounds, and thus the cost of a process for producing a HDS catalyst and also the time of said process is substantially reduced compare to conventional impregnation or sol-gel methods. Moreover, the single-pot method produces a catalyst that differs from catalysts obtained by traditional impregnation-based methods in terms of structure, morphology, and catalyst properties, for example, surface acidity, BET surface area, total pore volume, average pore size, desulfurization activity, etc.

In some preferred embodiments, the catalyst support mixture is mixed with a titanium source before mixing the first and the second metal precursors with the catalyst support mixture. Accordingly, the catalyst support of the HDS catalyst further contains titanium. The catalyst support mixture is stirred for at least 1 hour but preferably no more than 2 hours, after mixing the titanium source with the catalyst support mixture. Preferably, a molar ratio of silicon in the silica source to the titanium in the titanium source is in the range of 5:1 to 20:1, more preferably 8:1 to 15:1, most preferably about 10:1. Preferably, the titanium source is a titanium alkoxide. Examples of the titanium source that may be used include, but are not limited to, titanium isopropoxide, titanium ethoxide, titanium butoxide, etc. In another embodiment, the titanium source may be at least one solution containing a titanium salt selected from the group consisting of titanium oxysulfate, titanium fluoride, titanium chloride, titanium bromide, titanium iodide, titanium sulfate, and titanium carbonitride.

The single-pot method provides advantageous dispersion of the active catalyst materials on the catalyst support of the HDS catalyst, particularly for the HDS catalyst that is calcined at a temperature in the range of 250 to 350° C., preferably 290 to 325° C., preferably about 300° C., therefore, in one embodiment, the hydrothermal precursor does not include a complexing agent. In other words, mixing a complexing agent with the hydrothermal precursor can be eliminated from the single-pot method. The term "complexing agent" as used herein refers to a component that is used in conventional processes of making a catalyst to provide a good dispersion of active catalyst materials within a catalyst support. Exemplary complexing agents that may be excluded from mixing with the hydrothermal precursor include nitriloacetic acid, cyclohexanediaminetetraacetic acid, tris(2-aminoethyl)amine, triethylenetetraamine, diethylenetriaminepentaacetic acid, ethyleneglycol-bis-(beta-aminoethylether)-N,N'-tetraacetic acid, tetraethylenepentaamine, and derivatives thereof. However, in some embodiments, complexing agents such as citric acid, ethylenediaminetetraacetic acid (EDTA) and derivatives thereof such as N-hydroxy ethylenediaminetetraacetic acid or diammonium ethylenediaminetetraacetic acid may optionally be included in the hydrothermal precursor.

In some circumstances, complexing agents may provide stable complexes of active catalyst materials with metallic elements of the catalyst support, e.g. titanium or aluminum, and consequently provides stable HDS catalysts with longer life span. In view of that, in some embodiments, a complexing agent is mixed with the hydrothermal precursor prior to hydrothermal treating the hydrothermal precursor, for example during or after mixing the first and the second metal precursors. Preferably, the complexing agent is an aqueous citric acid solution having a concentration in the range of 1 to 5 M, preferably 1.5 to 4 M, preferably 2 to 3 M. Alternative complexing agents that may be used in these embodiments, include but are not limited to ethylenediaminetetraacetic acid (EDTA) and derivatives thereof such as N-hydroxy ethylenediaminetetraacetic acid or diammonium ethylenediaminetetraacetic acid. Other preferable complexing agents may include nitriloacetic acid (NTA), cyclohexanediaminetetraacetic acid, tris(2-aminoethyl) amine, triethylenetetraamine, diethylenetriaminepentaacetic acid, ethyleneglycol-bis-(beta-aminoethylether)-N,N'-tetraacetic acid, tetraethylenepentaamine, and the like. Varying amounts of complexing agents may be utilized depending on a number of factors such as solubility in the hydrothermal precursor, the type of the catalyst support, and the type of the active catalyst materials. Preferably, 0.01 to 0.5 gram, preferably 0.02 to 0.4 gram, preferably 0.03 to 0.3 gram, preferably 0.04 to 0.2 gram, preferably 0.05 to 0.1 gram of the complexing agent is mixed with one gram of the hydrothermal precursor. In a preferred embodiment, a weight ratio of the complexing agent to molybdenum in the hydrothermal precursor is in the range of 5:1 to 1:5, preferably 3:1 to 1:3, preferably 1.5:1 to 1:1.5, preferably about 1:1.

In one embodiment, a total cost of producing the HDS catalyst, as described in the first aspect, is at least 20%, preferably at least 30%, preferably at least 40%, preferably at least 50% lower than the total cost of an existing method of producing a hydrodesulfurization catalyst, particularly the methods wherein the active catalyst materials are introduced via an impregnation method after the formation of the catalyst support. The method of producing the HDS catalyst (also referred to as a "single-pot" method), as described in the first aspect, provides a simple route towards low-cost design and preparation of HDS catalysts.

According to a second aspect, the present disclosure relates to the hydrodesulfurization (HDS) catalyst that is produced with the method described in the first aspect.

The HDS catalyst includes a catalyst support, which comprises SBA-15 and preferably titanium. In the preferred embodiment where titanium is present in the catalyst support, a molar ratio of silicon in the SBA-15 to titanium is in a range of 5:1 to 20:1, preferably 6:1 to 15:1, preferably 8:1 to 12:1, preferably about 10:1. In addition to the catalyst support, the HDS catalyst further includes at least two active catalyst materials selected from groups 4 to 12 of the periodic table. Exemplary active catalyst materials include molybdenum, tungsten, nickel, cobalt, manganese, iron, copper, zinc, zirconium, niobium, ruthenium, rhodium, palladium, silver, gold, platinum, iridium, osmium, tantalum, and hafnium. However, in a preferred embodiment, said active catalyst materials are selected from groups 6, 9, and 10 of the periodic table. Accordingly, the active catalyst materials are preferably selected from the group consisting of nickel, molybdenum, cobalt, and tungsten, wherein the active catalyst materials are homogenously deposited on the catalyst support, as described previously. In some preferred embodiments, the active catalyst materials are nickel and molybdenum, or cobalt and tungsten.

In some embodiments, at least 50%, preferably at least 60%, preferably at least 70%, preferably at least 80%, preferably at least 90%, preferably at least 95%, preferably at least 99%, of the external surface area of the catalyst support is covered with a thin layer of the active catalyst materials, wherein the thin layer may have a uniform thickness of no more than 500 nm, preferably no more than 200 nm, preferably no more than 100 nm, preferably no more than 50 nm, preferably no more than 20 nm, preferably no more than 10 nm. In some embodiments, the HDS catalyst includes intra-crystalline pores and may also include inter-crystalline pores, and the active catalyst materials may be located at the inter-crystalline pores or preferably at the intra-crystalline pores. Said active catalyst materials may be present in elemental form, cationic forms, oxide forms, sulfide forms, etc. An amount of the active catalyst materials in the HDS catalyst may be in the range of 0.1 wt % to 15.0 wt %, preferably 0.5 wt % to 14.0 wt %, preferably 1.0 wt % to 13.0 wt %, with the weight percent being relative to the total weight of the HDS catalyst. In some embodiments, the HDS catalyst includes nickel and molybdenum, wherein a weight percent of nickel is in the range of 0.1 wt % to 5.0 wt %, preferably 0.5 wt % to 4.0 wt %, preferably about 1.0 wt % to about 3.0 wt %, and wherein a weight percent of molybdenum is in the range of 1.0 wt % to 15.0 wt %, preferably 5.0 wt % to 14.0 wt %, preferably about 10.0 wt % to about 13.0 wt %, each relative to the total weight of the HDS catalyst.

In some embodiments, the HDS catalyst has a surface acidity of at least 0.19 mmol/g, preferably in the range of 0.195 to 0.250 mmol/g, preferably in the range of 0.20 to 0.24 mmol/g, in accordance with a temperature-programmed desorption (TPD) method.

Accordingly, a predetermined amount of the HDS catalyst is pretreated at a temperature in the range of 500 to 700° C., preferably about 600° C. for 20 to 40 minutes, preferably 30 minutes in the presence of helium gas. Then, the HDS catalyst is cooled to a temperature in the range of 80 to 120° C., preferably about 100° C. in an atmosphere containing helium gas and 5 to 15 vol %, preferably 5 to 10 vol % of ammonia. After that, the HDS catalyst is heated at a temperature ramp rate of 10° C.·min$^{-1}$ from 100° C. to 800° C., wherein ammonia is desorbed, and the amount of desorbed ammonia (measured by a thermal conductivity detector (TCD)) is used to determine the surface acidity of the HDS catalyst.

In some embodiments, the HDS catalyst has a BET surface area of at least 300 m$^2$/g, preferably in the range of 350 to 550 m$^2$/g, more preferably in the range of 380 to 450 m$^2$/g. The HDS catalyst includes micro-pores (i.e. pores with an average pore diameters in the range of 1-40 nm, preferably 2-20 nm) having a micro/meso-pore BET surface area in the range of 20-35 m$^2$/g, preferably 22-33 m$^2$/g, more preferably 25-30 m$^2$/g. The HDS catalyst further includes macro-pores (i.e. pores with an average pore diameters of greater than 50 nm, preferably in the range of 40 to 100 nm, preferably 50 to 90 nm) having a macro-pore BET surface area in the range of 250-450 m$^2$/g, preferably 300-400 m$^2$/g, more preferably 320-380 m$^2$/g. The HIDS catalyst has a total micro/meso-pore volume in the range of from about 0.01 to about 0.02 cm$^3$/g, (cubic centimeter per gram of the HDS catalyst) preferably from about 0.012 to about 0.016 cm$^3$/g. Also, a total macro-pore volume of the HDS catalyst is in the range of from about 0.4 to about 1.0 cm$^3$/g, preferably from about 0.45 to about 0.75 cm$^3$/g. Therefore, the LIDS catalyst has a total pore volume (i.e. micro/meso-pore volume and macro-pore volume) in the range from about 0.4 to about 1.0 cm$^3$/g, preferably 0.45 to about 0.8 cm$^3$/g, preferably 0.5 to about 0.75 cm$^3$/g. Furthermore, the HDS catalyst has an average pore size in the range of 5 to 8 nm, preferably 5.5 to 7.5 nm, preferably 6.0 to 7.0 nm.

In some embodiments, a nano-cubical flat-sheet morphology of the active catalyst materials is present on at least a portion of the external surface area of the HDS catalyst. Accordingly, at least 50%/c, preferably at least 60%, preferably at least 70%, preferably at least 80%, preferably at least 90%, preferably at least 95%, preferably at least 99%/o, of the external surface area of the catalyst support, i.e. SBA-15 or titanium-modified SBA-15, is covered with the nano-cubical flat-sheet morphology of the active catalyst materials.

The HDS catalyst may be in the form of pellets or particulates having a diameter in the range of 100 μm to 1.0 mm, preferably 200 μm to 800 μm, more preferably 300 μm to 700 μm. The HDS catalyst may also be extrudated to have one or more geometries including, for example, cylindrical, rectilinear, star-shaped, conical, pyramidal, rectangular, cubical, and ring-shaped geometries.

According to a third aspect, the present disclosure relates to a method of hydro-desulfurizing a hydrocarbon feedstock by contacting the hydrocarbon feedstock with the HDS catalyst in the presence of hydrogen gas.

The hydrocarbon feedstock may be delivered from a hydrocarbon reservoir or directly from an offshore or an onshore well. For example, the hydrocarbon feedstock may be a crude oil that is produced from an oil well, particularly from a sour gas oil well. Alternatively, the hydrocarbon feedstock may be a gaseous stream that is supplied directly from an offshore or an onshore well, or a sulfur-containing liquid or gaseous stream, e.g. gaseous ethane, liquid gasoline, liquid naphtha, etc. in a refinery or a petrochemical plant that needs to be desulfurized.

The hydrocarbon feedstock includes one or more sulfur-containing hydrocarbon compounds and may also include various hydrocarbon compounds such as $C_{1-50}$ hydrocarbon compounds, preferably $C_{1-30}$ hydrocarbon compounds, preferably $C_{1-20}$ hydrocarbon compounds, depending on the origin of the hydrocarbon feedstock. In one embodiment, the hydrocarbon feedstock includes $C_{1-20}$ normal paraffins, e.g. $C_{1-20}$ alkanes, $C_{1-20}$ isoparaffins, $C_{1-20}$ cycloparaffins (i.e. naphthenes) or $C_{1-20}$ cycloparaffins having side chain alkyl groups, $C_{1-20}$ aromatics or $C_{1-20}$ aromatics with side chain alkyl groups. The hydrocarbon feedstock may include no more than 5.0 wt %, preferably no more than 2.0 wt %, preferably no more than 1.0 wt %, preferably no more than 0.5 wt %, preferably no more than 0.4 wt %, preferably no more than 0.3 wt % of the sulfur-containing hydrocarbon compounds, with each weight percent being relative to the total weight of the hydrocarbon feedstock. In a preferred embodiment, the hydrocarbon feedstock may include diolefin (diene) compounds, e.g. propadiene, butadiene, and/or pentadiene, and the method involves separating the diolefin (diene) compounds or reducing a content of the diolefin (diene) compounds to a value below 0.5 wt %, preferably below 0.1 wt %, relative to the total weight of the hydrocarbon feedstock, before contacting the hydrogen feedstock with the HDS catalyst. Since the diolefin compounds are highly polymerizable, the presence of the diolefin compounds may poison the HDS catalyst. In one embodiment, the hydrocarbon feedstock is in a gaseous state and may contain less than 5.0 vol %, preferably less than 2.0 vol % of nitrogen and water vapor, relative to the total volume of the hydrocarbon feedstock. Further to the above, the hydrocarbon feedstock may include traces amount (preferably less than 0.1 vol %) of argon, helium, and nitrogen oxides (i.e. nitric oxide, nitrous oxide, nitrogen dioxide).

In one embodiment, the sulfur-containing hydrocarbon compounds is one or more of mercaptans, sulfides, disulfides, polysulfides, thiols, thioethers, thioesters, thioacetals, sulfoxides, sulfones, thiosulfonates, sulfimides, sulfoximides, sulfonediimines, s-nitrosothiols, sulfur halides, thioketones, thioaldehydes, thiocarbonyls, sulfur oxides, thiocarboxylic acids, thioamides, sulfonic acid, sulfinic acid, sulfenic acids, sulfonium, oxosulfonium, sulfuranes, and persulfuranes. In a preferred embodiment, the sulfur-containing hydrocarbon compound is at least one compound selected from the group consisting of a thiophene, a benzothiophene, a dibenzothiophene, an alkyl benzothiophene, an alkyl dibenzothiophene, a dialkyl dibenzothiophene, and a tetrahydrothiophene. Preferably, the sulfur-containing hydrocarbon compound is at least one compound selected from the group consisting of dibenzo[b,d]thiophene, 5-methyl-1-benzothiophene, 4-methyldibenzo[b,d]thiophene, and 4,6-dimethyldibenzo[b,d]thiophene.

Accordingly, the hydrocarbon feedstock is contacted with the HDS catalyst in the presence of hydrogen gas under favorable reaction conditions to hydro-desulfurize the sulfur-containing hydrocarbon compounds present in the hydrogen feedstock, and to form hydrogen sulfide and a hydro-desulfurized hydrocarbon compounds. In a preferred embodiment, the hydrocarbon feedstock is contacted with the HDS catalyst at a temperature in the range of 200 to 500° C., preferably 250 to 450° C., preferably 300 to 400° C., preferably about 350° C., wherein a pressure of the hydrogen gas is in the range of 2 to 10 MPa, preferably 3 to 8 MPa, preferably 4 to 6 MPa, preferably about 5 MPa. For example, in some embodiments, the hydrocarbon feedstock includes dibenzothiophene and dodecane, wherein the hydrocarbon feedstock is contacted with the HDS catalyst at a temperature in the range of 250 to 450° C., preferably 300 to 400° C., and a pressure in the range of 4 to 6 MPa, preferably about 5 MPa to hydro-desulfurize at least a portion of dibenzothiophene to form biphenyl and/or cyclohexyl benzene as well as hydrogen sulfide. Since the hydrocarbon feedstock may be supplied from a hydrocarbon reservoir or directly from an offshore or an onshore well, therefore in circumstances where a temperature or a pressure of the hydrocarbon feedstock falls outside of the above ranges, the temperature and the pressure of the hydrocarbon feedstock may be adjusted to be within the above mentioned ranges prior to contacting the hydrocarbon feedstock with the HDS catalyst.

Figure 30:
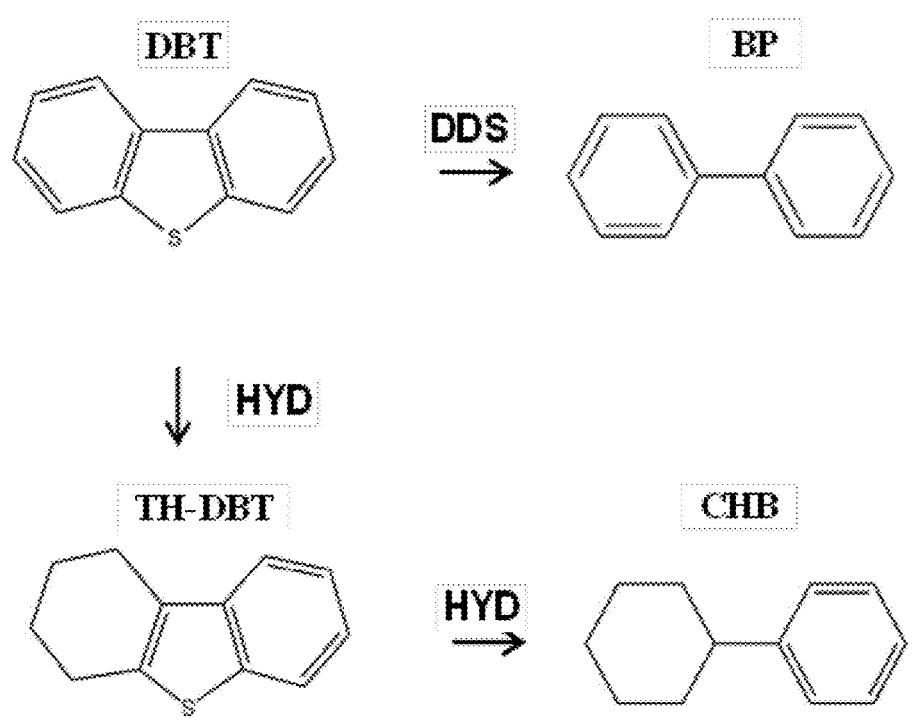
FIG. 30 represents two reaction pathways for the hydrodesulfurization of dibenzothiophene.

In some embodiments, the sulfur-containing hydrocarbon compounds present in the hydrogen feedstock are hydro-desulfurized via more than one reaction pathways, preferably two reaction pathways; i) a direct desulfurization reaction (DDS) or a hydrogenolysis, whereby C—S bonds are cleaved in a single reaction step, ii) a hydrogenation reaction (HYD), wherein a complex is formed by hydrogenation of the sulfur-containing hydrocarbon compound in a first reaction step, and the C—S bonds of the complex are cleaved in a subsequent reaction step. These reaction pathways are shown in FIG. 30. Accordingly, the HDS catalyst has a rate constant ratio, i.e. $k_{DDS}/k_{HYD}$, in the range of 7 to 22, preferably 8 to 20, preferably 10 to 18, preferably about 17.5. The term "$k_{DDS}$" refers to a rate constant of the direct desulfurization reaction with the HDS catalyst, which is in the range of $5 \times 10^{-3}$ to $30 \times 10^{-3}$ 1/min, preferably about $20 \times 10^{-3}$ 1/min. Also, the term "$k_{HYD}$" refers to a rate constant of the hydrogenation reaction with the HDS catalyst, which is in the range of $0.5 \times 10^{-3}$ to $3.0 \times 10^{-3}$ 1/min, preferably about $1.5 \times 10^{-3}$ 1/min.

A volumetric flow ratio of the hydrogen gas to the hydrocarbon feedstock may vary depending on the type of sulfur-containing hydrocarbon compounds present in the hydrocarbon feedstock. In some embodiments, the volumetric flow ratio of the hydrogen gas to the hydrocarbon feedstock is in the range of 100:1 to 1:100, preferably 80:1 to 1:80, preferably 50:1 to 1:50, preferably 40:1 to 1:40, preferably 30:1 to 1:30.

The hydrocarbon feedstock may be in a liquid state or a gaseous state. In view of that, contacting the hydrocarbon feedstock with the HDS catalyst may be different, depending on the state of the hydrocarbon feedstock, i.e. the liquid state or the gaseous state. In one embodiment, the hydrocarbon feedstock is in a liquid state or in a gaseous state and the hydrocarbon feedstock is passed through the HDS catalyst, for example via a fixed-bed or a fluidized-bed reactor. In another embodiment, the hydrocarbon feedstock is in a gaseous state and the hydrocarbon feedstock is passed over the HDS catalyst, or may stay stagnant over the HDS catalyst, i.e. as an atmosphere to the catalyst. Yet in another embodiment, the hydrocarbon feedstock is in a liquid state and the hydrocarbon feedstock is mixed with the HDS catalyst to form a heterogeneous mixture, for example in a batch reactor equipped with a rotary agitator.

In one embodiment, a concentration of sulfur-containing hydrocarbon compounds in the hydrocarbon feedstock is no more than 50,000 ppm, preferably no more than 20,000 ppm, preferably no more than 10,000 ppm, preferably no more than 5,000 ppm, preferably no more than 4,000 ppm, preferably no more than 3,000. In an alternative embodiment, a concentration of sulfur-containing hydrocarbon compounds in the hydrocarbon feedstock is in the range of 100 to 10,000 ppm, preferably 500 to 8,000 ppm, preferably 1,000 to 6,000 ppm, preferably 1,500 to 5,000 ppm, preferably 2,000 to 3,000 ppm. The concentration of sulfur-containing hydrocarbon compounds in the hydrocarbon feedstock may be reduced by at least 50%, preferably at least 60%, preferably by about 70% to about 90%, more preferably by about 75% to about 85%, after 1 hour of contacting the hydrocarbon feedstock with the HDS catalyst. For example, in one embodiment, an initial concentration of sulfur-containing hydrocarbon compounds in the hydrocarbon feedstock prior to contacting with the HDS catalyst is in the range of 1,500 to 5,000 ppm, preferably 2,000 to 3,000 ppm, wherein this concentration is reduced to a value in the range of 400 to 650 ppm, preferably 450 to 550 ppm, after 1 hour of contacting the hydrocarbon feedstock with the HDS catalyst. The concentration of sulfur-containing hydrocarbon compounds in said hydrocarbon feedstock may further be reduced to a value in the range of 10 to 50 ppm, preferably 15 to 40 ppm, after 4 hours of contacting. In some embodiments, the hydrocarbon feedstock is contacted with the HDS catalyst for no more than 6 hours. Accordingly, a ratio of a concentration of the sulfur-containing hydrocarbon compound in the hydrocarbon feedstock after the contacting to the concentration of the sulfur-containing hydrocarbon compound in the hydrocarbon feedstock before the contacting is in the range of 1:10 to 1:1,000, preferably 1:50 to 1:500, preferably 1:60 to 1:400, preferably 1:80 to 1:200, preferably about 1:100.

In a preferred embodiment, the HDS catalyst is treated with a gaseous mixture that contains hydrogen gas prior to contacting with the hydrocarbon feedstock. Preferably, the HDS catalyst is treated with the gaseous mixture at a temperature in the range of 300 to 500° C., preferably 350 to 450° C., preferably about 400° C., for 1 to 6 hours, preferably about 2 to 3 hours. In a preferred embodiment, the gaseous mixture is passed through the HDS catalyst, wherein the gaseous mixture contains 2 to 10 vol %, preferably 4 to 6 vol % of hydrogen gas diluted in helium and/or argon, with the volume percent being relative to the total volume of the gaseous mixture. This optionally preferred step may reduce at least a portion of active catalyst materials to their corresponding metallic forms.

In another preferred embodiment, the HDS catalyst is presulfided after being treated with the gaseous mixture and before being contacted with the hydrocarbon feedstock. Preferably, the HDS catalyst is presulfided with a sulfide-containing solution at a temperature in the range of 250 to 450° C., preferably 300 to 400° C., preferably about 350° C. The sulfide-containing solution preferably includes carbon disulfide ($CS_2$), and may further include one or more of dimethyl disulfide, ethylene sulfide, trimethylene sulfide, propylene sulfide, and bis(methylthio)methane. This step may convert active catalyst materials in oxide form to their corresponding sulfide form, since the active catalyst materials in sulfide form may be catalytically more active than in oxide form.

In some embodiments, the HDS catalyst is treated with an organic solvent and/or thermally treated to regenerate the HDS catalyst. "Regenerating the HDS catalyst" as used herein refers to a process whereby sulfur compounds that are not converted during the hydro-desulfurizing process are removed from the external surface of the HDS catalyst, and the HDS catalyst is prepared to be utilized in a subsequent hydro-desulfurizing process.

The hydrogen sulfide, which is produced during hydro-desulfurizing the sulfur-containing hydrocarbon compounds, may be collected and further supplied to a sulfur manufacturing plant to produce sulfur.

The examples below are intended to further illustrate protocols for the HDS catalyst, the method of producing the HDS catalyst, and the method of using the HDS catalyst in a hydrodesulfurization process, and are not intended to limit the scope of the claims.

Example 1—Materials

Tetraethylorthosilicate (TEOS) $(CH_5O)_4Si$ as the silica source, pluronic P123 $PEO_{20}$—$PPO_{70}$-$PEO_{20}$ triblock copolymer as the structural directing agent, nickel nitrate hexahydrate (99%) as the nickel precursor, titanium isopropoxide (97%) as the titanium source, citric acid (99.7%), dibenzothiophene (DBT) (98%), and dodecane were procured from Sigma-Aldrich and used as received without additional purification. Ammonium molybdate (VI) tetrahydrate (99%) was obtained from ACROS organis and used as received without additional purification. High-purity deionized water (18 μS/cm) was produced in-hous using a Thermo Scientific Barnstead NANOPURE after distillation with a Labstrong FiSTREEM™ II 2S Glass Still distiller.

Example 2—Synthesis of SBA-15 and Titanium-Modified SBA-15 Support and Impregnation of NiMo Active Phase on the Support Mesoporous SBA-15 and Ti-SBA-15 (Si/Ti=10) were prepared using procedures described by Castano, et al. via the hydrothermal (HT) synthesis method [D. Zhao, J. Feng, Q. Huo, N. Melosh, G. H. Fredrickson, B. F. Chmelka, G. D. Stucky, Triblock Copolymer Syntheses of Mesoporous Silica with Periodic 50 to 300 Angstrom Pores, Science, 279 (1998) 548-552]. Typically, SBA-15 was prepared from a reaction mixture of 60 g of 2 M HCl, 4.16 g of TEOS, 2 g of P123, and 15 g of deionized water stirred at 500 rpm for 24 hours at 40° C. The mixture was transferred into a Teflon-lined autoclave and then heated for 24 hours according to the hydrothermal method. The synthesized SBA-15 was calcined at 550° C. for 6 hours (ramp rate of 10° C./min) for template removal. For Ti-SBA-15, the same procedure was followed but with the incorporation of an equivalent amount of titanium isopropoxide to the mixture after stirring the TEOS-surfactant mixture for 90 minutes.

The impregnation of a NiMo active phase on the support was performed by the excess wet solution method in deionized water. The procedure involves stirring equivalent amounts of nickel and molybdenum precursors (to obtain 3 wt. % and 13 wt. % of metal, respectively, 20 in the catalyst) at room temperature for 3 hours with or without citric acid, followed by the addition of 1 g of the Ti-SBA-15 to the mixture. This mixture was stirred for 2 hours and then dried by slow evaporation at 60-70° C. prior to a final calcination at 300° C. or 550° C., the catalyst was dried at 100° C. for 12 hours.

Example 3—Single-Pot (SP) Synthesis of Ti-SBA-15-NiMo Catalyst

The single-pot (SP) synthesis of HDS catalyst was accomplished by modifying the sol-gel preparation route for SBA-15. FIG. 1 is schematic representation illustrating the single-pot (SP) synthesis of NiMo supported on metal-modified SBA-15 catalysts. This method involves the addition of approximately 4.16 g of TEOS to a mixture containing a well-dispersed surfactant (P123) in 2 M HCl and deionized water, which was stirred for 30 minutes. The titanium precursor in a 10:1 (Si:Ti) molar ratio was added before the hydrolysis of TEOS and stirred continuously for 20 hours. A mixture of the Mo and Ni (13 wt. % and 3 wt. %, respectively) precursors, which were previously mixed at room temperature (RT) for 1 hour, was added to the synthesis pot and stirred vigorously for 3 hours at room temperature. The mixture was transferred to a Teflon-lined autoclave for hydrothermal (HT) synthesis at 100° C. for 24 hours. The solid product was then centrifuged and washed with deionized water before drying at 100° C. for 12 hours and subjected to a final calcination at either 300° C. or 550° C. for 6 hours in a muffle furnace. The heating rate during calcination was maintained at 10° C./min.

Table 1 lists the supports and catalyst prepared and investigated in this disclosure along with their codes and descriptions. The Ti-SBA-15-NiMo catalysts prepared by the single-pot meth with and without a complexing agent are denotes as TSMN(CA)-SP(x) and TSMN-SP(x), respectively, where x represents the calcination temperature. The Ti-SBA-15/NiMo catalysts prepared by the impregnation method with and without a complexing agent are denoted as TSMN(CA)-Imp(x) and TSMN-Imp(x), respectively, where x represents the calcination temperature.

TABLE 1

Description of supports and catalysts.

| Sample Code | Description | Catalyst Preparation Method | Calcination Temperature (° C.) |
|---|---|---|---|
| SBA-15 | Template-free SBA-15 | — | 550 |
| Ti-SBA-15 | Titanium-modified SBA-15 | — | 550 |
| TSMN-Imp300 | NiMo/Ti-SBA-15 | Impregnation | 300 |
| TSMN-Imp550 | NiMo/Ti-SBA-15 | Impregnation | 550 |
| TSMN-SP300 | NiMo-Ti-SBA-15 | Single-Pot | 300 |
| TSMN-SP550 | NiMo-Ti-SBA-15 | Single-Pot | 550 |
| TSMN(CA)-Imp300 | NiMo/Ti-SBA-15 with citric acid | Impregnation | 300 |
| TSMN(CA)-Imp550 | NiMo/Ti-SBA-15 with citric acid | Impregnation | 550 |
| TSMN(CA)-SP300 | NiMo-Ti-SBA-15 with citric acid | Single-Pot | 300 |
| TSMN(CA)-SP550 | NiMo-Ti-SBA-15 with citric acid | Single-Pot | 550 |

Example 4—Analysis of the Textural Properties of Synthesized Catalysts

The BET surface area, pore size, and pore volumes of the synthesized catalysts were measured on a Micrometrics ASAP 2020 using $N_2$ adsorption-desorption at −196° C. Prior to measurement, the samples were degassed at 250° C. for 3 hours to remove impurities or moisture. The Brunauer-Emmett-Teller (BET) method was used to calculate the surface areas and the Barret-Joyner-Halenda (BJH) method was used to calculate the pore size distribution.

Figure 2:
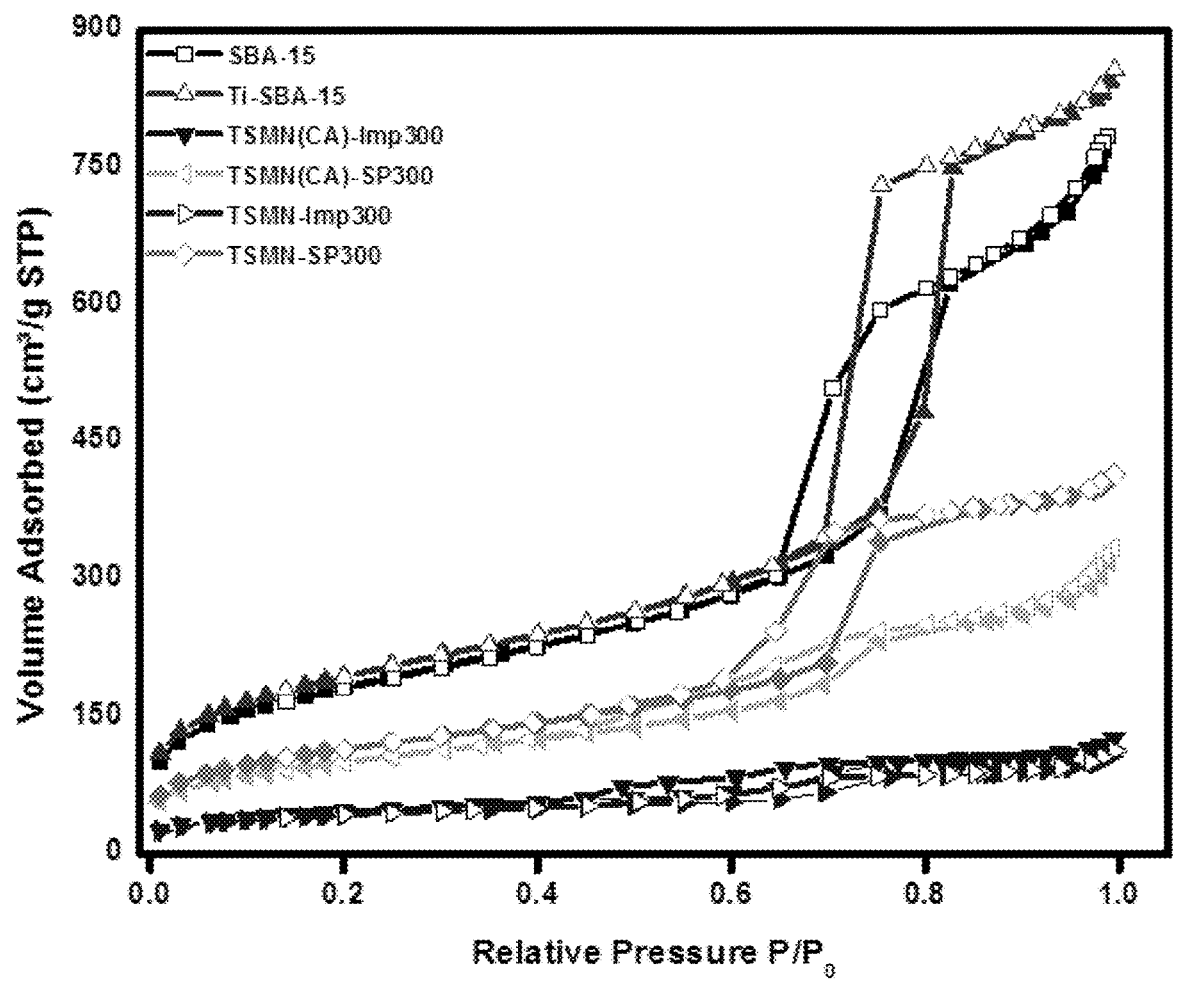
FIG. 2 represents nitrogen adsorption-desorption isotherms of different HDS catalysts calcined at 300° C.
Figure 3:
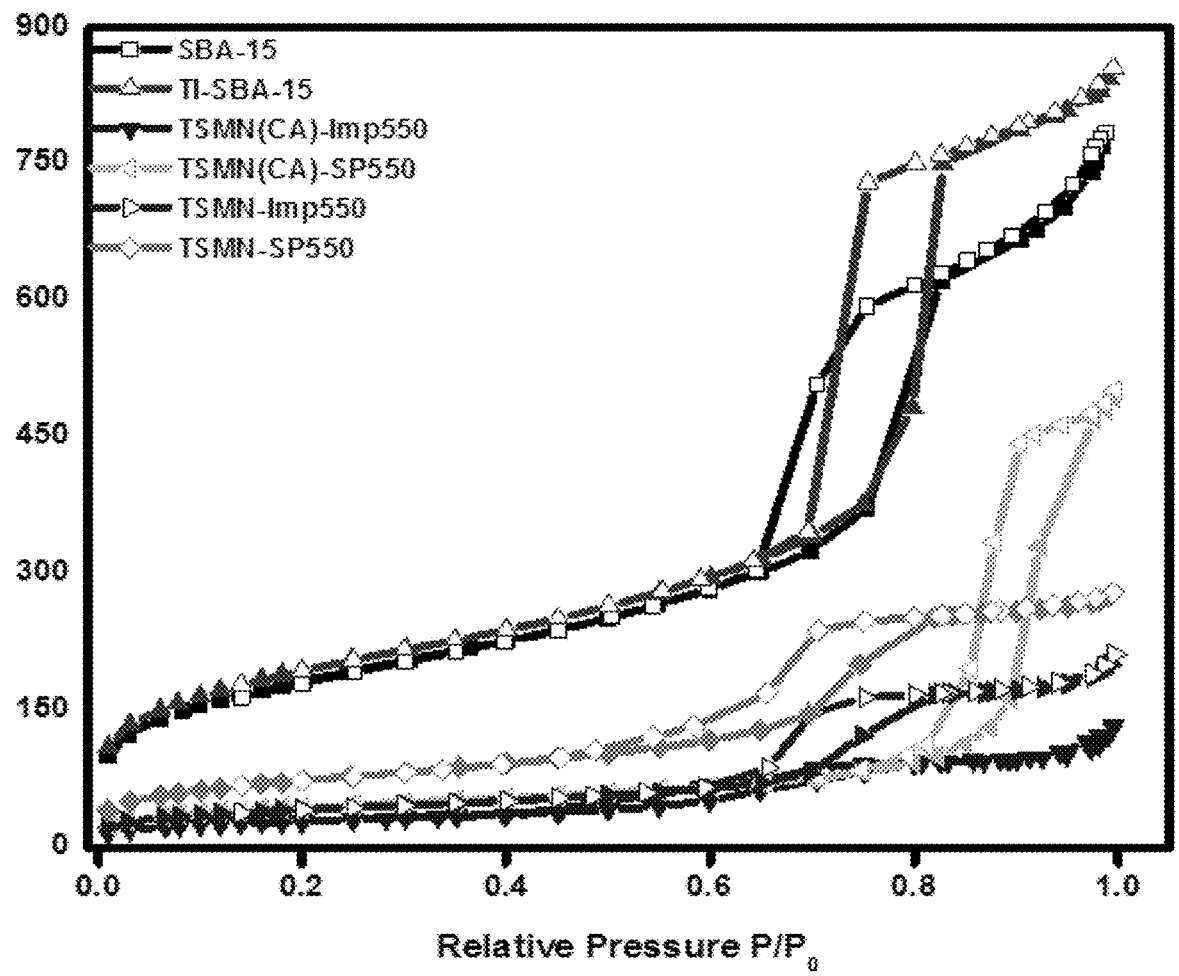
FIG. 3 represents nitrogen adsorption-desorption isotherms of different HDS catalysts calcined at 550° C.

Table 2 presents the textural properties of synthesized supports (SBA-15 and Ti-modified SBA-15) and NiMo catalysts without sulfidation. FIG. 2 presents the adsorption-desorption isotherms of NiMo catalysts calcined at 300° C. FIG. 3 presents the adsorption-desorption isotherms of NiMo catalysts calcined at 550° C. The parent SBA-15 exhibits a high specific surface area (643 $m^2/g$) and large pore volume (1.25 $cm^3/g$), with an average pore diameter of 7.9 nm. It exhibits a type-IV isotherm showing an H1 hysteresis loop, which is a typical characteristic of mesoporous SBA-15 silica according to IUPAC. Further, SBA-15 combines micro and mesopores with uniform hexagonal tunable mesopores (~4-14 nm). Notably, the incorporation of titanium into SBA-15 improves its textural properties (for example, the surface area is increased to 679 $m^2/g$). The introduction of Ni and Mo onto Ti-SBA-15 either by impregnation or through the single-pot approach; however, reduces the pore size due to surface and void blockage. The catalysts prepared by the SP approach exhibit higher surface areas than those prepared by the impregnation method. The relative preservation of textural properties by the SP approach is likely due to the ability of the active metal-oxides to be embedded into the support matrix without surface coverage. Also, the SP approach provides a highly dispersed active phase for efficient catalytic performance.

TABLE 2

Textural properties of supports and catalysts.

| Sample Code | BET Surface Area (m²/g) | Microporous Surface Area (m²/g) | Macroporous Surface Area (m²/g) | Microporous Pore Volume (cm³/g) | Total Pore Volume (cm³/g) | Average Pore Size (nm) |
|---|---|---|---|---|---|---|
| SBA-15 | 643 | 47 | 595 | 0.023 | 1.25 | 7.9 |
| Ti-SBA-15 | 679 | 81 | 596 | 0.040 | 1.39 | 8.3 |
| TSMN-Imp300 | 146 | 21 | 125 | 0.011 | 0.16 | 6.1 |
| TSMN-Imp550 | 145 | 21 | 125 | 0.010 | 0.33 | 8.8 |
| TSMN-SP300 | 403 | 30 | 374 | 0.014 | 0.66 | 6.5 |
| TSMN-SP550 | 260 | 17 | 244 | 0.008 | 0.45 | 6.6 |
| TSMN(CA)-Imp300 | 160 | 14 | 146 | 0.007 | 0.19 | 5.5 |
| TSMN(CA)-Imp550 | 103 | 11 | 92 | 0.005 | 0.21 | 7.6 |
| TSMN(CA)-SP300 | 352 | 28 | 324 | 0.013 | 0.51 | 6.3 |
| TSMN(CA)-SP550 | 155 | 18 | 137 | 0.009 | 0.77 | 6.9 |

Example 5—Thermogravimetric Analysis (TGA) of Synthesized Catalysts

The thermal stability of the synthesized catalysts was evaluated by thermogravimetric analysis (TGA) in which weight loss or phase change is observed upon heating the catalyst samples to 1000° C. Thermal analysis of the prepared catalysts was performed on an SDTQ600 TGA in high-purity zero air. The furnace temperature was increased from 30° C. to 1000° C. at a rate of 10° C./min, whereas the cooling rate was 30° C./min. SBA-15 has been reported to possess higher hydrothermal stability due to the thick microporous silica pore wall (~3-6 nm) compared to MCM-41, MCM-48, and HMS [K. Cassiers, T. Linssen, M. Mathieu, M. Benjelloun, K. Schrijnemakers, P. Van Der Voort, P. Cool, E. Vansant, A detailed study of thermal, hydrothermal, and mechanical stabilities of a wide range of surfactant assembled mesoporous silicas, Chemistry of materials, 14 (2002) 2317-2324].

Figure 4:
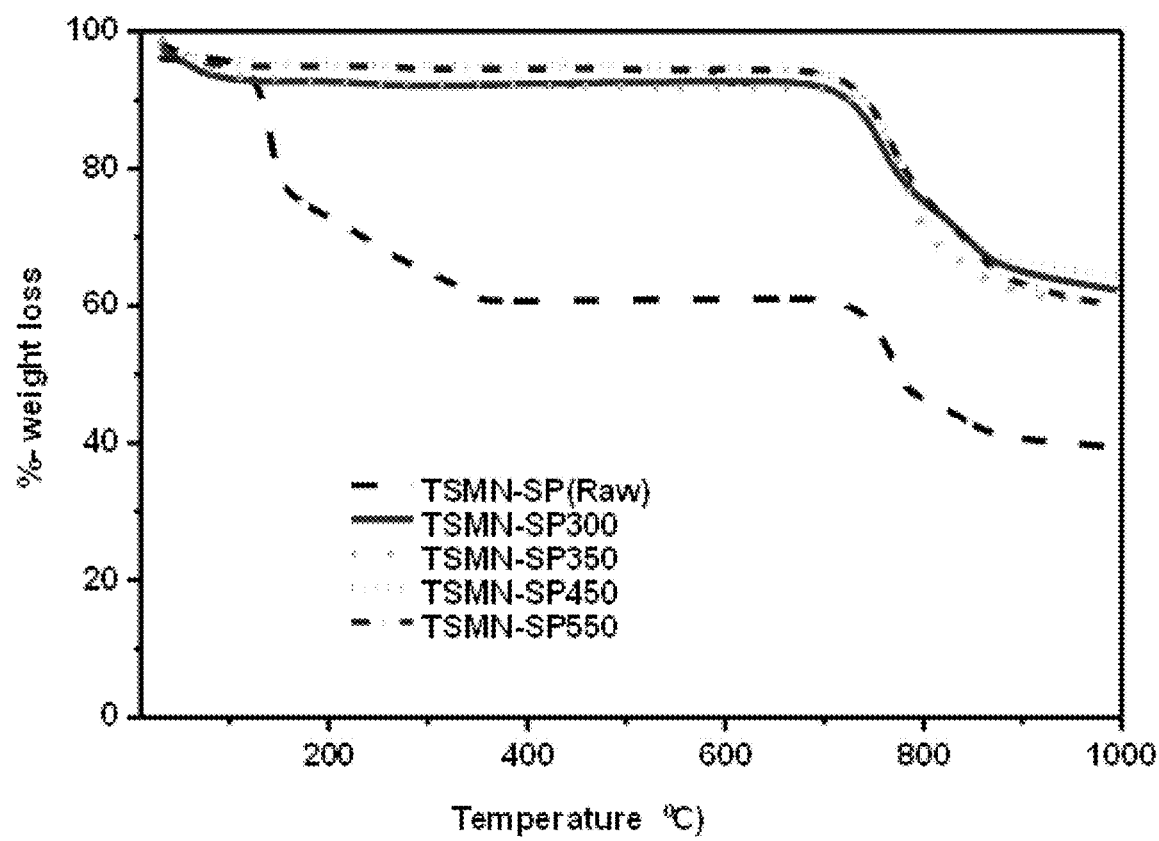
FIG. 4 represents the thermogravimetric analysis of different HDS catalysts that are produced via the single-pot method and are calcined at different temperatures.

FIG. 4 shows the thermogravimetric analysis (TGA) of catalyst prepared by the single-pot (SP) method and calcined at different temperatures and without calcination (raw). The TGA of the TSMN catalyst sample without calcination reveals that the major weight loss occurs below 300° C. due to the loss of surfactants and adsorbed water. FIG. 4 shows this. When the catalysts that were calcined at different temperatures between 300° C. and 550° C. were subjected to TGA, the results show similar trends in the thermal stability up to 700° C. FIG. 4 shows this. Therefore, a calcination temperature of 300° C. is sufficient to remove surfactants and adsorbed water from the catalysts synthesized by the single-pot (SP) method.

Example 6—X-Ray Diffraction (XRD) Analysis of Synthesized Catalysts

Figure 5:
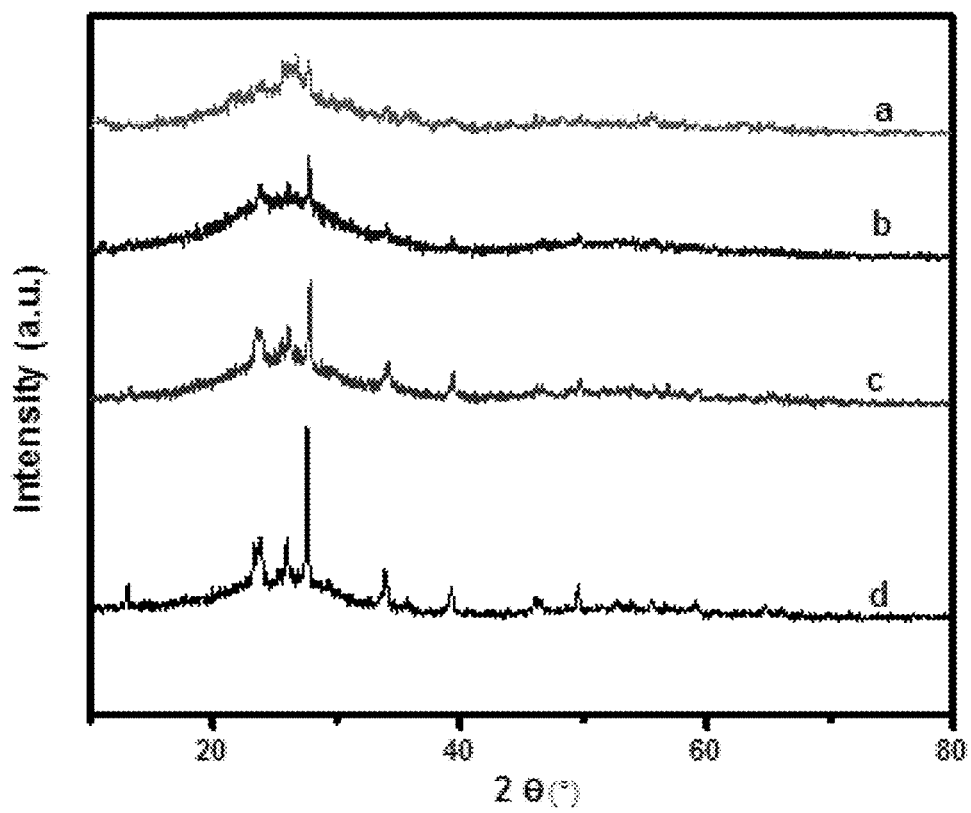
FIG. 5 represents X-ray Diffraction spectra of different HDS catalysts calcined at 300° C., including (a) TSMN-Imp300, (b) TSMN(CA)-Imp300, (c) TSMN-SP300, and (d) TSMN(CA)-SP300.
Figure 6:
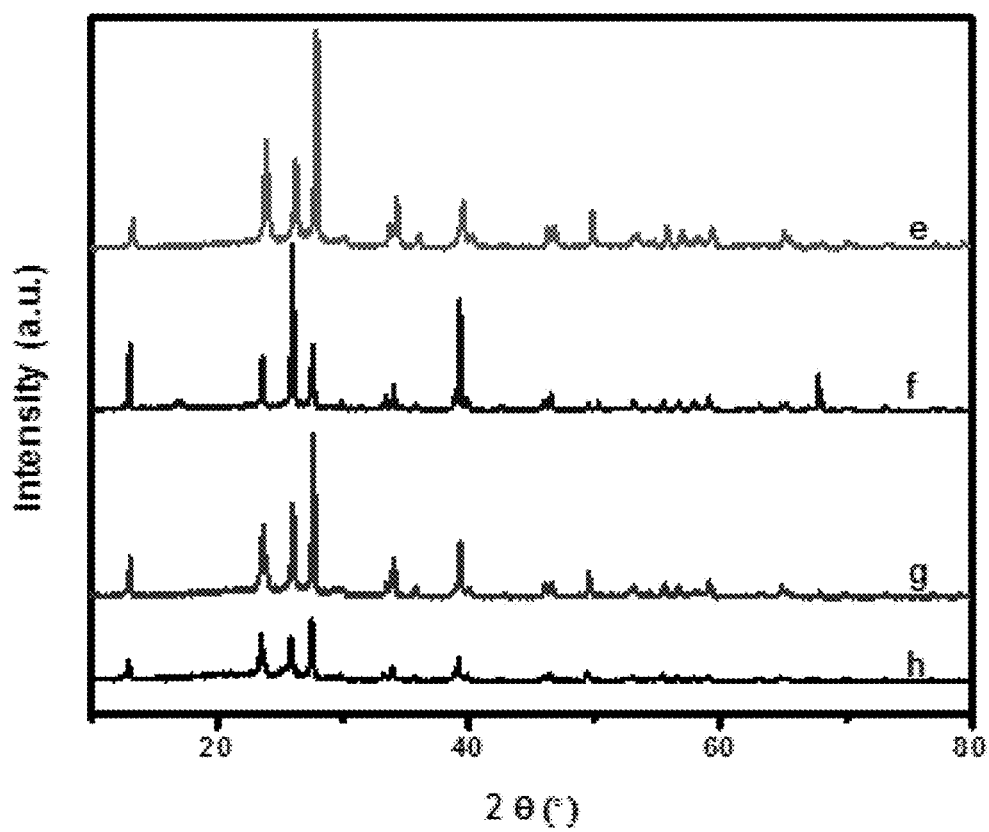
FIG. 6 represents X-ray Diffraction spectra of different HDS catalysts calcined at 550° C., including (e) TSMN-Imp550, (f) TSMN(CA)-Imp550, (g) TSMN-SP550, and (h) TSMN(CA)-SP550.

X-ray powder diffraction (XRD) analysis enabled the determination of the crystallinity and different phases of the synthesized supports (SBA-15 and Ti-SBA-15) and the NiMo catalysts supported on Ti-SBA-15. X-ray diffraction (XRD) at a wide angle using Cu anode (9 kV) at Kα=1.5405 (Rigaku miniflex-bench top X-ray powder) was used to determine the crystallinity of the prepared catalysts. The samples were scanned between 20° and 80° at 3°/min. FIG. 5 is the X-ray diffraction analysis of the HDS catalysts calcined at 300° C. including TSMN-Imp300 (a), TSMN (CA)-Imp300 (b), TSMN-SP300 (c), and TSMN(CA)-SP300 (d). FIG. 6 is the X-ray diffraction analysis of HDS catalysts calcined at 550° C. including TSMN-Imp550 (e), TSMN(CA)-Imp550 (f), TSMN-SP550 (g), and TSMN (CA)-SP550 (h). FIG. 5 and FIG. 6 show that the structure of SBA-15 in low-angle XRD exhibits three characteristic diffraction peaks of silica. The peaks are associated with p6 mm ordered hexagonal symmetry, indexed as (100), (110), and (200) [Z. Jin, X. Wang, X. Cui, Synthesis and morphological investigation of ordered SBA-15-type mesoporous silica with an amphiphilic triblock copolymer template under various conditions, Colloids and Surfaces A: Physicochemical and Engineering Aspects, 316 (2008) 27-36]. Additionally, the $MoO_3$ XRD characteristic peaks are identified at different peak positions. The main peaks at 2-theta of 13, 23.42, 26, 27.52, and 39 degrees are due to the orthorhombic $MoO_3$ crystalline phase, whereas peaks at 2-theta of 26, 39, and 67, which mostly coincide with and are overlaid by MoO3, indicate $TiO_2$ anatase [S. Badoga, R. V. Sharma, A. K. Dalai, J. Adjaye, Hydrotreating of heavy gas oil on mesoporous zirconia supported NiMo catalyst with EDTA, Fuel, 128 (2014) 30-38; and H. Sun, C. Wang, S. Pang, X. Li, Y. Tao, 1H. Tang, M. Liu, Photocatalytic TiO 2 films prepared by chemical vapor deposition at atmosphere pressure, Journal of Non-Crystalline Solids 354 (2008) 1440-1443]. The diffraction peak associated with nickel could not be identified due to concentration limitations in XRD for metal oxides.

The molybdena present in all catalysts subjected to high temperature calcination can be indexed to orthorhombic $MoO_3$ (JCPDS card no. 05-0508) with the space group Pbnm of octahedral form. However, the orientations or phases are different from one another. FIG. 6 shows the catalyst prepared by impregnation with a complexing agent (TSMN (CA)-Imp550, (e)) at a higher calcination temperature shows exceptional characteristics of $MoO_3$ reflections unlike others, due to high intensity of the peak centered at 2θ=26 degrees. The catalysts obtained by the single-pot (SP) approach (TSMN-SP550 (g) and TSMN(CA)-SP550 (h)) exhibit more $MoO_2$ reflections by the reduction of the peak intensity, like due to a greater interaction with SBA-15 in the preparation method [P. Delporte, C. Pham-Huu, P. Vennegues, M. J. Ledoux, J. Guille, Physical characterization of molybdenum oxycarbide catalyst; TEM, XRD and XPS, Catalysis today, 23 (1995) 251-267]. In general, the catalysts calcined at 300° C. show better dispersion on the support with broadened peaks and low intensities of the (020), (040), and (060) phases, signifying the presence of small crystallites [O. Y. Gutiérrez, F. Perez, G. A. Fuentes, X. Bokhimi, T. Klimova, Deep HDS over NiMo/Zr-SBA-15 catalysts with varying MoO 3 loading, Catalysis Today 130 (2008) 292-301].

Example 7—Raman Spectrometry Analysis of Synthesized Catalysts

Raman spectrometry is a non-destructive method for characterizing the dispersion of active metal on the support [W. Li, G. D. Meitzner, R. W. Borry, E. Iglesia, Raman and X-ray absorption studies of Mo species in Mo/H-ZSM5 catalysts for non-oxidative CH 4 reactions, Journal of Catalysis, 191 (2000) 373-383]. A Raman spectrometer (HORIBA, iHR320 with CCD detector) with a laser wavelength of 532 nm (300 mW, green laser) was used to characterize the $MoO_3$ and $TiO_2$ phases. Molybdenum oxide and titanium oxide phases for the HDS NiMo catalysts were examined using a laser Raman spectrometer, with the crystalline molybdena existing either in the tetrahedral (tet) or octahedral (oct) form [Y. V. Plyuto, I. Babich, I. Plyuto, A. Van Langeveld, J. Moulijn, Synthesis and characterization of molybdenum (VI) oxo-species on the surface of fumed alumina and silica, Colloids and Surfaces A: Physicochemical and Engineering Aspects, 125 (1997) 225-230]. For pure $MoO_3$ crystallites, the peaks at 819 and 665 $cm^{-1}$ are characteristic of the Mo—O—Mo bridge stretching mode, wheras symmetric stretching of the Mo=O terminal oxygen is observed at 994 $cm^{-1}$ [G. Mestl, P. Ruiz, B. Delmon, H. Knozinger, Oxygen-exchange properties of MoO3: an in situ Raman spectroscopy study, The Journal of Physical Chemistry, 98 (1994) 11269-11275; and B. C. Windom, W. Sawyer, D. W. Hahn, A Raman spectroscopic study of MoS2 and MoO3: applications to tribological systems, Tribology Letters, 42 (2011) 301-310]. The bands at 336 $cm^{-1}$ and 375 $cm^{-1}$ could be assigned to the bending and deformation modes of vibrations of O=Mo=O and O—Mo—O, and the Mo—O wagging mode of vibration is observed at 280-290 $cm^{-1}$ [M. Py, P. E. Schmid, J. Vallin, Raman scattering and structural properties of MoO3, II Nuovo Cimento B (1971-1996), 38 (1977) 271-279; and M. Dieterle, G. Weinberg, G. Mestl, Raman spectroscopy of molybdenum oxides Part I. Structural characterization of oxygen defects in MoO 3-x by DR UV/VIS, Raman spectroscopy and X-ray diffraction, Physical Chemistry Chemical Physics, 4 (2002) 812-821].

Figure 7:
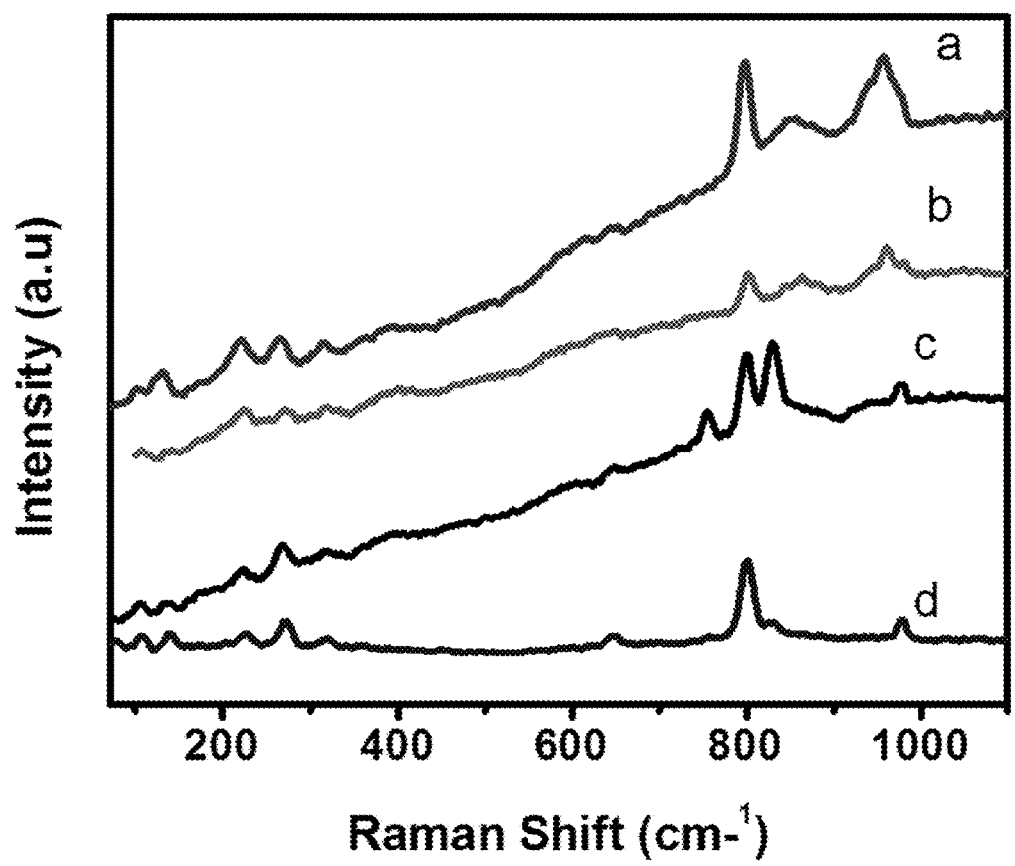
FIG. 7 represents Raman spectra of different HDS catalysts calcined at 300° C., including (a) TSMN-Imp300, (b) TSMN(CA)-Imp300, (c) TSMN-SP300, and (d) TSMN (CA)-SP300.
Figure 8:
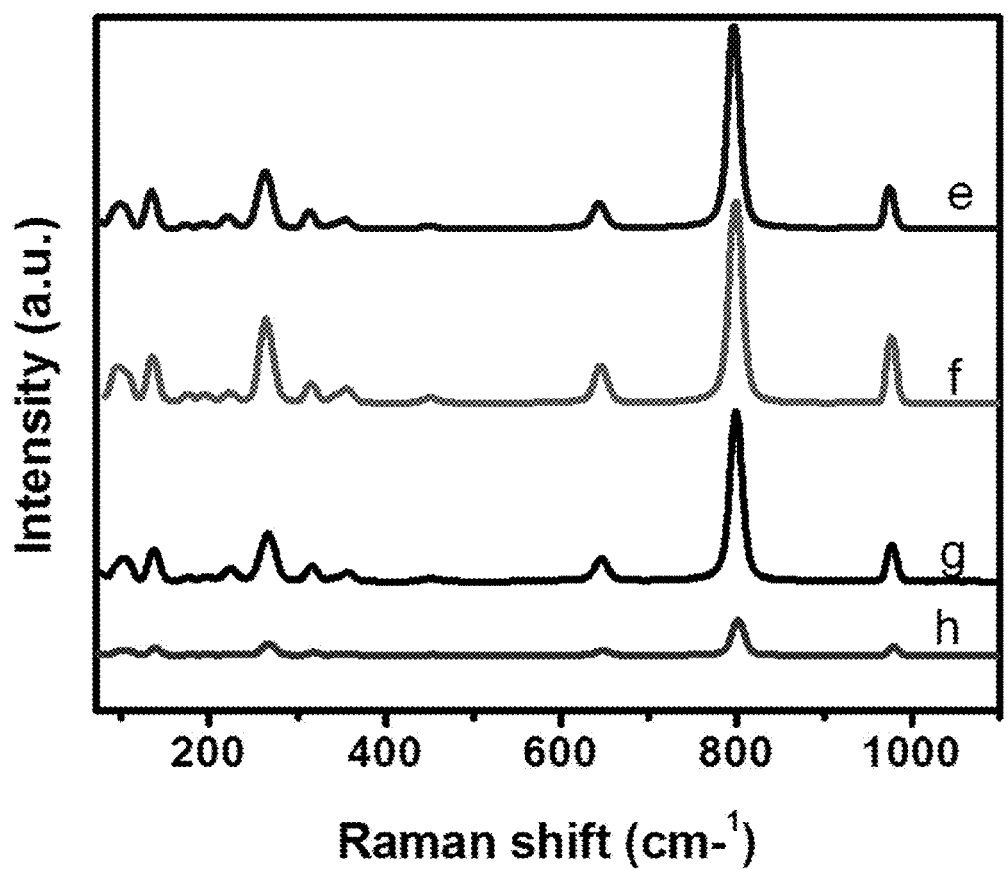
FIG. 8 represents Raman spectra of different HDS catalysts calcined at 550° C., including (e) TSMN-Imp550, (f) TSMN(CA)-Imp550, (g) TSMN-SP550, and (h) TSMN (CA)-SP550.

FIG. 7 is the Raman spectra of the HDS catalysts calcined at 300° C. including TSMN-Imp300 (a), TSMN(CA)-Imp300 (b), TSMN-SP300 (c), and TSMN(CA)-SP300 (d). FIG. 8 is the Raman spectra of HDS catalysts calcined at 550° C. including TSMN-Imp550 (e), TSMN(CA)-Imp550 (f), TSMN-SP550 (g), and TSMN(CA)-SP550 (h). FIG. 7 and FIG. 8 show that the characteristic $MoO_3$ peaks are observed in all NiMo catalysts prepared at the higher calcination temperature (550° C.), with differences in their peak intensities and positions likely due to different degrees of interactions with the supports (related to the degree of crystallinity and/or dispersion). The dominant molybdena species due to the interaction on SBA-15 may exist in the form of tetrahedral $(Si—O—)_2Mo(=O)_2$ di-oxo species, due to the presence of bands at 970 $cm^{-1}$ and 355 $cm^{-1}$ [K. Amakawa, P. Hildebrandt, R. Schlögl, R. Schomäcker, C. Limberg, Active site for propene metathesis in silica-supported molybdenum oxide catalysts, in, Technische Universitat Berlin, 2013]. However, good dispersion is achieved for the NiMo oxide catalysts subjected to a lower calcination temperature, as evidenced by the presence of amorphous peaks at 950 $cm^{-1}$ [S. Braun, L. G. Appel, V. L. Camorim, M. Schmal, Thermal spreading of MoO3 onto silica supports, The Journal of Physical Chemistry B, 104 (2000) 6584-6590].

Figure 9:
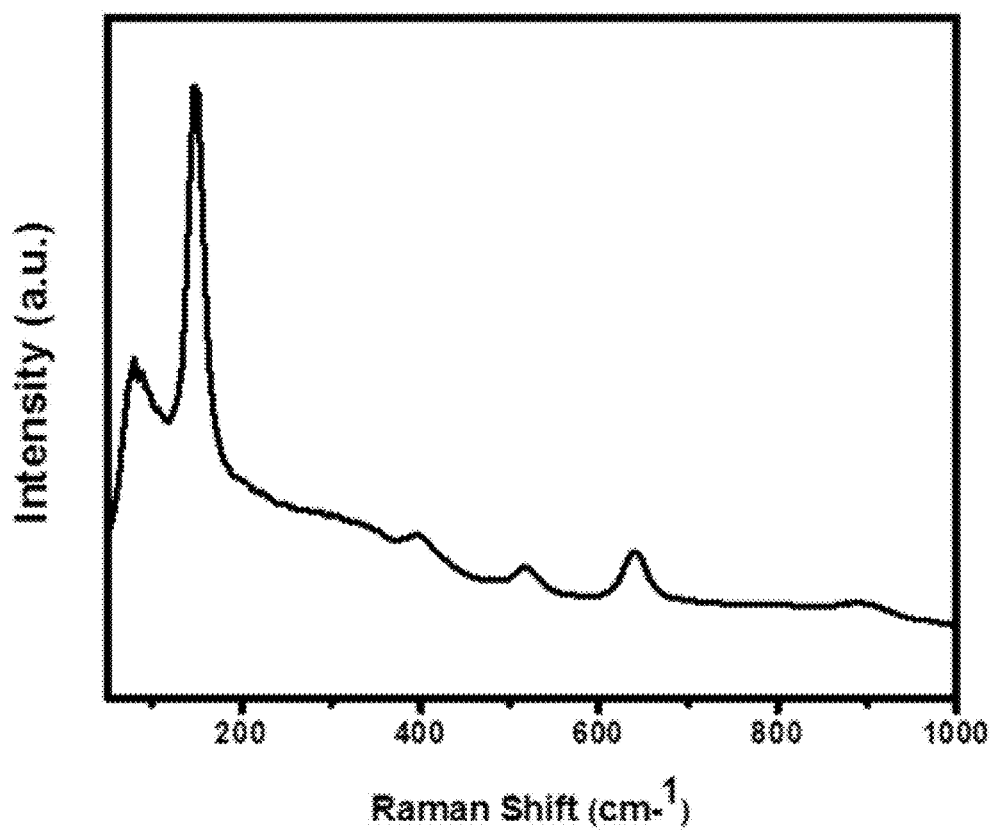
FIG. 9 represents a Raman spectrum of a catalyst support of the HDS catalyst, having SBA-15 and titanium, with Anatase mode of vibrations.

Notably, Ti-SBA-15 synthesized by the direct approach before the addition of NiMo for the HDS oxide catalysts exhibits five peaks corresponding to the anatase phase of titania. Peak analysis reveals that the stretching ($E_g$) mode of vibrations in O—Ti—O is observed at 144, 197, and 630 $cm^{-1}$, whereas the symmetric ($B_{1g}$) and asymmetric ($A_{1g}$) bending vibrations are at 395 and 520 $cm^{-1}$, respectively [S. Maity, M. Rana, S. Bej, J. Ancheyta-Juarez, G. M. Dhar, T. P. Rao, Studies on physico-chemical characterization and catalysis on high surface area titania supported molybdenum hydrotreating catalysts, Applied Catalysis A: General, 205 (2001) 215-225]. However, upon the introduction of Mo into the matrix support, all modes of vibrations assigned to titania (anastase) become unobservable, perhaps due to the dominance of Mo. FIG. 9 is the Raman spectra of Ti-SBA-15 with anastase mode of vibrations.

Therefore, the observed peaks in FIG. 7 and FIG. 8 are assigned only to $MoO_x$ phases of either crystalline single-pot (SP) or impregnation HDS catalysts.

Figure 10:
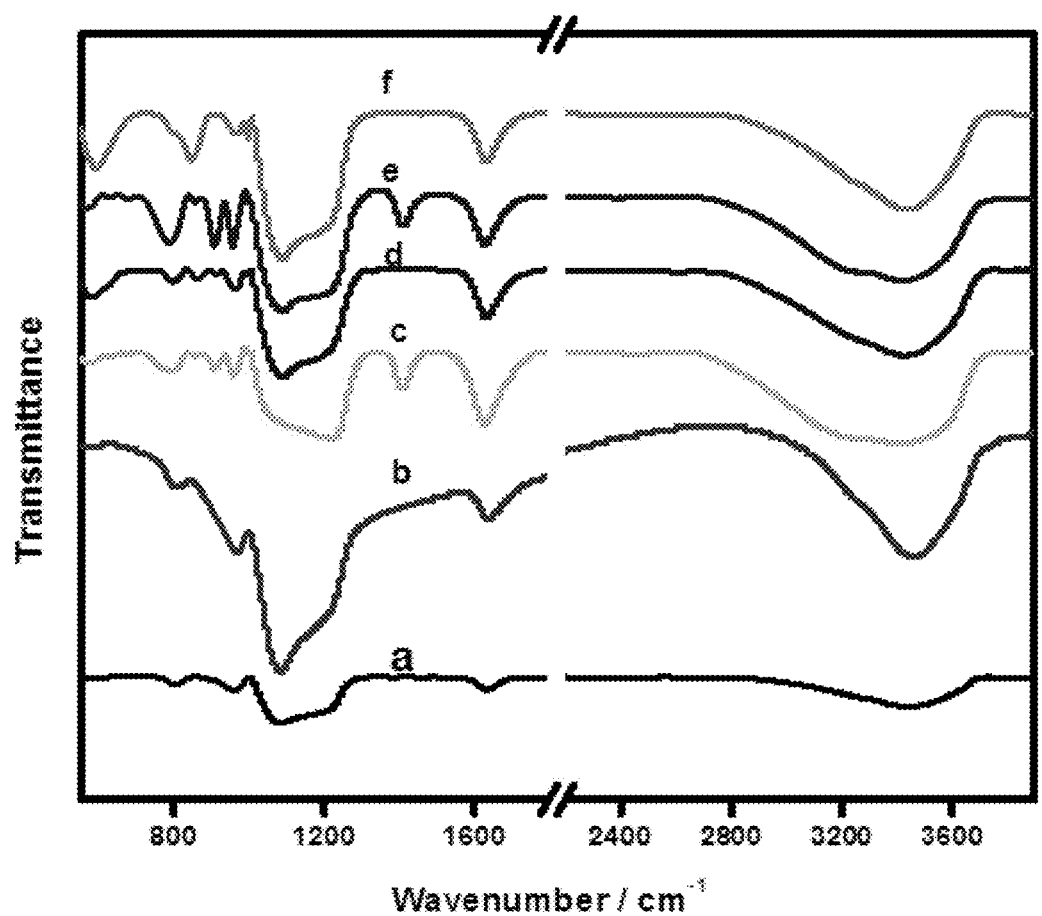
FIG. 10 represents FTIR spectra of different catalyst supports and also different HDS catalysts calcined at 300° C., including (a) SBA-15, (b) Ti-SBA-15, (c) TSMN-Imp300, (d) TSMN(CA)-Imp300, (e) TSMN-SP300, and (f) TSMN(CA)-SP300.
Figure 11:
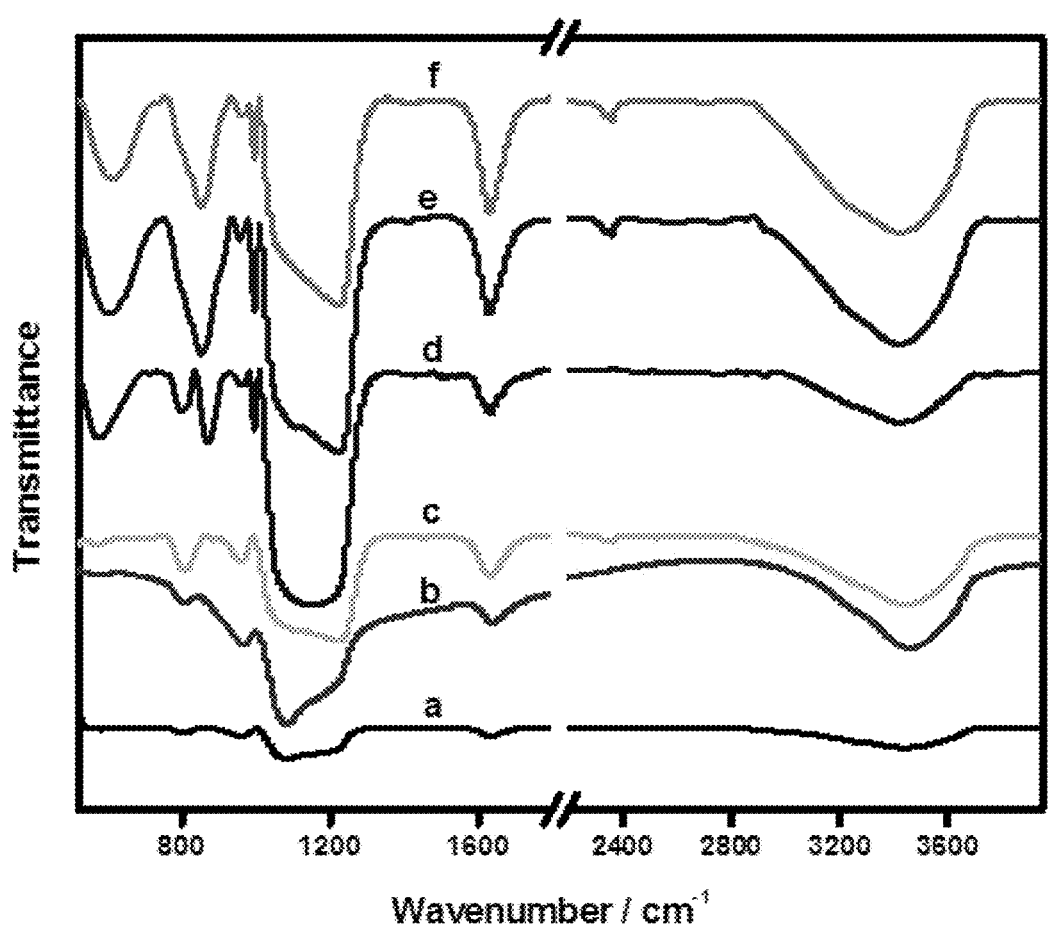
FIG. 11 represents FTIR spectra of different catalyst supports and also different HDS catalysts calcined at 550° C., including (a) SBA-15, (b) Ti-SBA-15, (c) TSMN-Imp550, (d) TSMN(CA)-Imp550, (e) TSMN-SP550, and (f) TSMN(CA)-SP550.

Example 8—Fourier Transformation Infrared (FTIR) Spectroscopy Analysis of Synthesized Catalysts Fourier-transform infrared (FTIR) was used to identify the functional groups present in the developed supports and catalysts. The infrared (IR) absorption spectra of SBA-15, Ti-SBA-15, and NiMo-supported catalysts were recorded on a Thermo Scientific Nicolet 6700 FT-IR spectrometer with a scanning range of 400-4000 cm-1. The samples for FTIR analysis were prepared using KBr powder mixed with the support/catalyst in a ratio of 100:1 to form pellet-like translucent discs. FTIR spectroscopy was used to gain insight into the functional groups of SBA-15, Ti-SBA-a5, and NiMo-modified Ti-SBA-15 catalysts. FIG. 10 is the FTIR results of the supports SBA-15 (a) and Ti-SBA-15 (b) and the HDS catalysts calcined at 300° C. including TSMN (CA)-Imp300 (c), TSMN(CA)-SP300 (d), TSMN-Imp300 (e), and TSMN-SP300 (f). FIG. 11 is the FTIR results of the supports SBA-15 (a) and Ti-SBA-15 (b) and the HDS catalysts calcined at 550° C. including TSMN(CA)-Imp550 (c), TSMN(CA)-SP550 (d), TSMN-Imp550 (e), and TSMN-SP550 (f).

As shown in FIG. 10 and FIG. 11, SBA-15 shows a strong intensity band at approximately 1218 $cm^{-1}$, corresponding to the asymmetric stretching modes of Si—O—Si, along with a broad absorption band at 1628 $cm^{-1}$, which is characteristic of the —OH stretching of an absorbed water molecule [L. Y. Lizama, T. E. Klimova, SBA-15 modified with Al, Ti, or Zr as supports for highly active NiW catalysts for HDS, Journal of materials science, 44 (2009) 6617-6628]. The band at 3500 $cm^{-1}$ can be associated with the silanol end group (Si—OH) and $Si_3$—O—Ti—OH due to Bronsted acid sites. The incorporation of Ti into the SBA-15 mesoporous silica network results in bands at 800 $cm^{-1}$ and 950 $cm^{-1}$ due to the Ti—O symmetric stretching mode and Ti—O—Si bending modes, respectively. For NiMo-supported SBA-15, the Mo—O—Mo stretching modes is observed at approximately 620 $cm^{-1}$ and 850 $cm^{-1}$, and the band at 797 $cm^{-1}$ corresponds to the presence of polymolybdate ($Mo_{36}$) [Z. Han, W. Pei, J. Xie, Y. Zou, X.-M. Ren, Two {Mo 36)}-containing polymolybdates: Synthesis, crystal structures, and spectral characterizations, Inorganic Chemistry Communications, 16 (2012) 61-64]. The intensity of this band is more pronounced for the catalysts synthesized with a complexing agent and calcined at 300° C., indicating better dispersion of the active metals. These results are in agreement with those obtained with Raman spectrometry and XRD analysis.

Example 9—Temperature-Programmed Desorption of Ammonia ($NH_3$-TPD) and Temperature-Programmed Reduction by Hydrogen (TPR-$H_2$) Analysis of the Synthesized Catalysts Surface acidity measurement was conducted on a Micromeritics Chemisorb 2750 (pulse chemisorption system) using 10 wt. % $NH_3$ by temperature-programmed desorption (TPD). Approximately 100 mg of non-sulfided catalyst was loaded into a quartz tube and covered with quartz. The sample was purged with high purity helium at 600° C. and held for 30 minutes before being cooled to 100° C. The probe molecule ($NH_3$) was adsorbed on the sample at 100° C. for 30 minutes, which was followed by helium purging for 60 minutes to remove any physisorbed ammonia. $NH_3$ desorption was accomplished by heating the furnace at 10° C./min to 800° C., and the data were recorded with a thermal conductivity detector.

Figure 12:
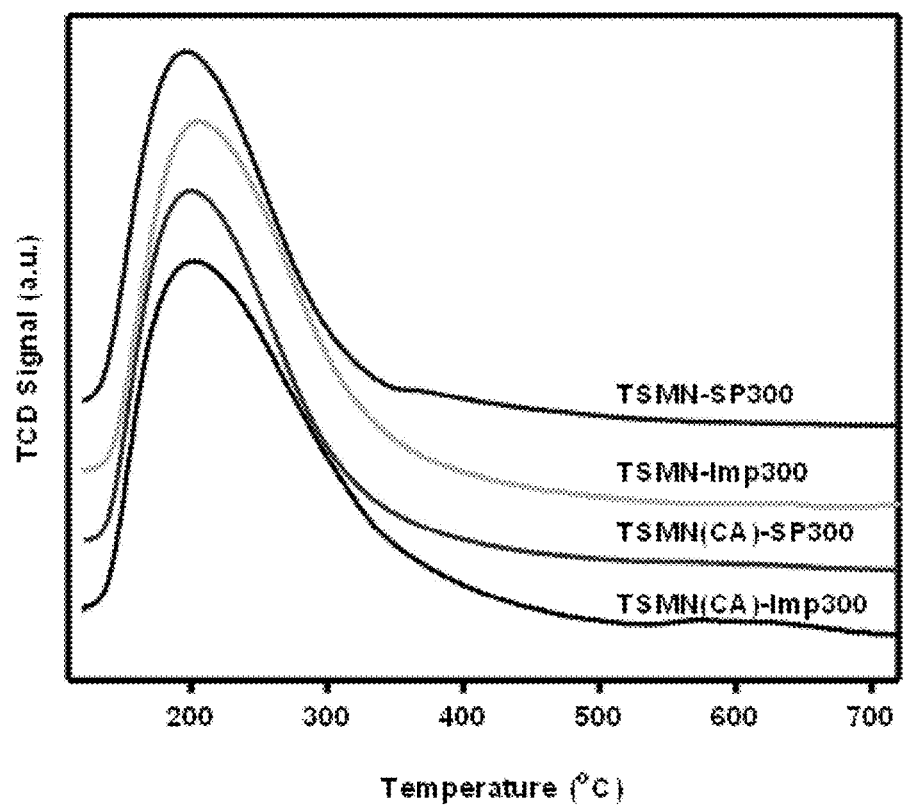
FIG. 12 represents the results of temperature-programmed desorption of ammonia (NH$_3$-TPD) for different HDS catalysts (in oxide form) calcined at 300° C.
Figure 13:
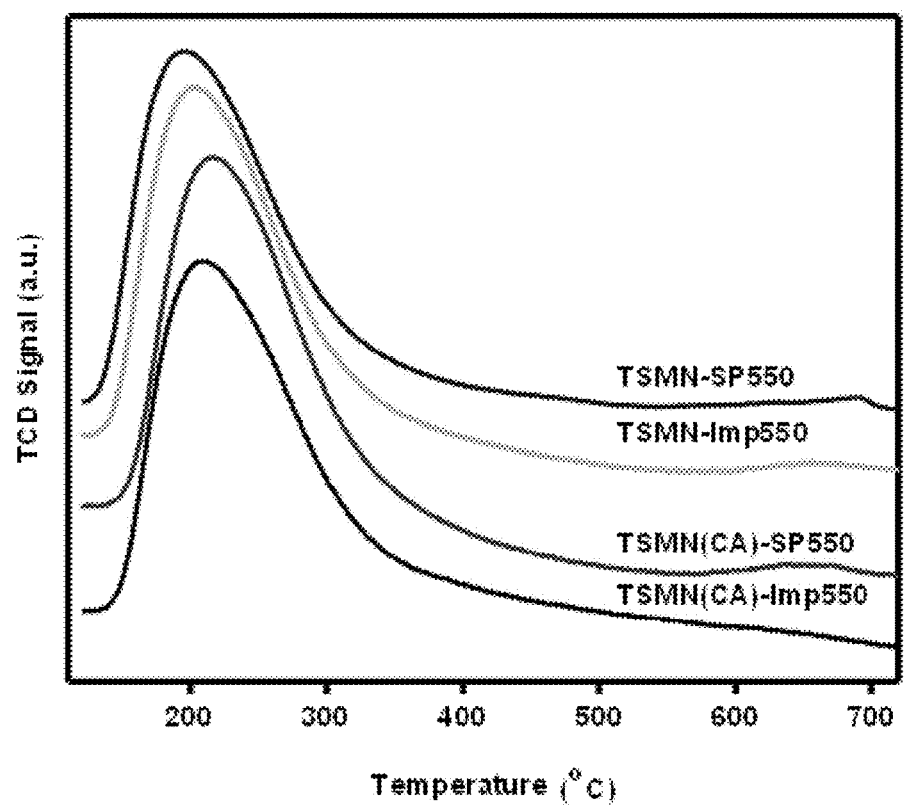
FIG. 13 represents the results of temperature-programmed desorption of ammonia (NH$_3$-TPD) for different HDS catalysts (in oxide form) calcined at 550° C.

The surface acidity characteristics of non-sulfided HDS catalysts were determined by $NH_3$-TPD. Titanium (Ti), which is a tetravalent element, incorporates into the silica framework easily, and the nature of the acidity observed in all prepared catalyst is mostly weak and/or moderate, characterized by Lewis acid sites in the temperature range between 195° C. and 220° C. FIG. 12 is the temperature-programmed desorption of ammonia ($NH_3$-TPD) results of the HDS (in the oxide form) calcined at 300° C. FIG. 13 is the temperature-programmed desorption of ammonia ($NH_3$-TPD) results of the HDS (in the oxide form) calcined at 550° C. Table 3 is the temperature-programmed desorption (TPD) and temperature-programmed reduction (TPR) results of the prepared catalysts (in the oxide form). In all cases, the acidic strength of catalysts calcined at 300° C. is higher than the catalysts calcined at 550° C. In addition, the catalysts prepared by the single-pot (SP) approach with or without citric acid [TSMN(CA)-SP300 and TSMN-SP300] have more surface acidity than others. It seems that the incorporation of active metals at the beginning of catalyst preparation in the single-pot (SP) approach improves the acidity considerably.

TABLE 3

TPD and TPR results of catalysts (in the oxide form).

| Catalysts | TPD: $NH_3$ desorbed | | TPR: $H_2$-consumption | |
|---|---|---|---|---|
| | Peak Temperature(s) (° C.) | Amount (mmol/g) | Peak Temperature(s) (° C.) | Amount (mmol/g) |
| TSMN-Imp300 | 206 | 0.158 | 640.57 | 29.49 |
| TSMN-Imp550 | 202 | 0.085 | 720, 1000 | 66.43 |
| TSMN-SP300 | 195 | 0.198 | 571, 950 | 44.22 |
| TSMN-SP550 | 196, 686 | 0.179 | 516, 888 | 27.34 |
| TSMN(CA)-Imp300 | 200 | 0.138 | 608, 1000 | 44.14 |
| TSMN(CA)-Imp550 | 207 | 0.100 | 590 | 45.44 |
| TSMN(CA)-SP300 | 202 | 0.235 | 471.47 | 43.74 |
| TSMN(CA)-SP550 | 218, 670 | 0.099 | 573, 1000 | 46.69 |

The reducibility potential of metal oxides supported on Ti-SBA-15 was determined by temperature-programmed reduction with hydrogen as the probe molecule using a Micromeritics (Autochem II-290) chemisorption analyzer. Approximately 50 mg of the prepared catalyst previously calcined at 300° C. or 550° C. were pre-treated for one hour in high-purity helium at 500° C. and then cooled to ambient temperature before being heated to 1000° C. at 10° C./min under a steady flow (20 mL/min) of 10% $H_2$ in helium. The consumption of $H_2$ at the reducible temperature(s) was recorded on a thermal conductivity detector (TCD).

Figure 14:
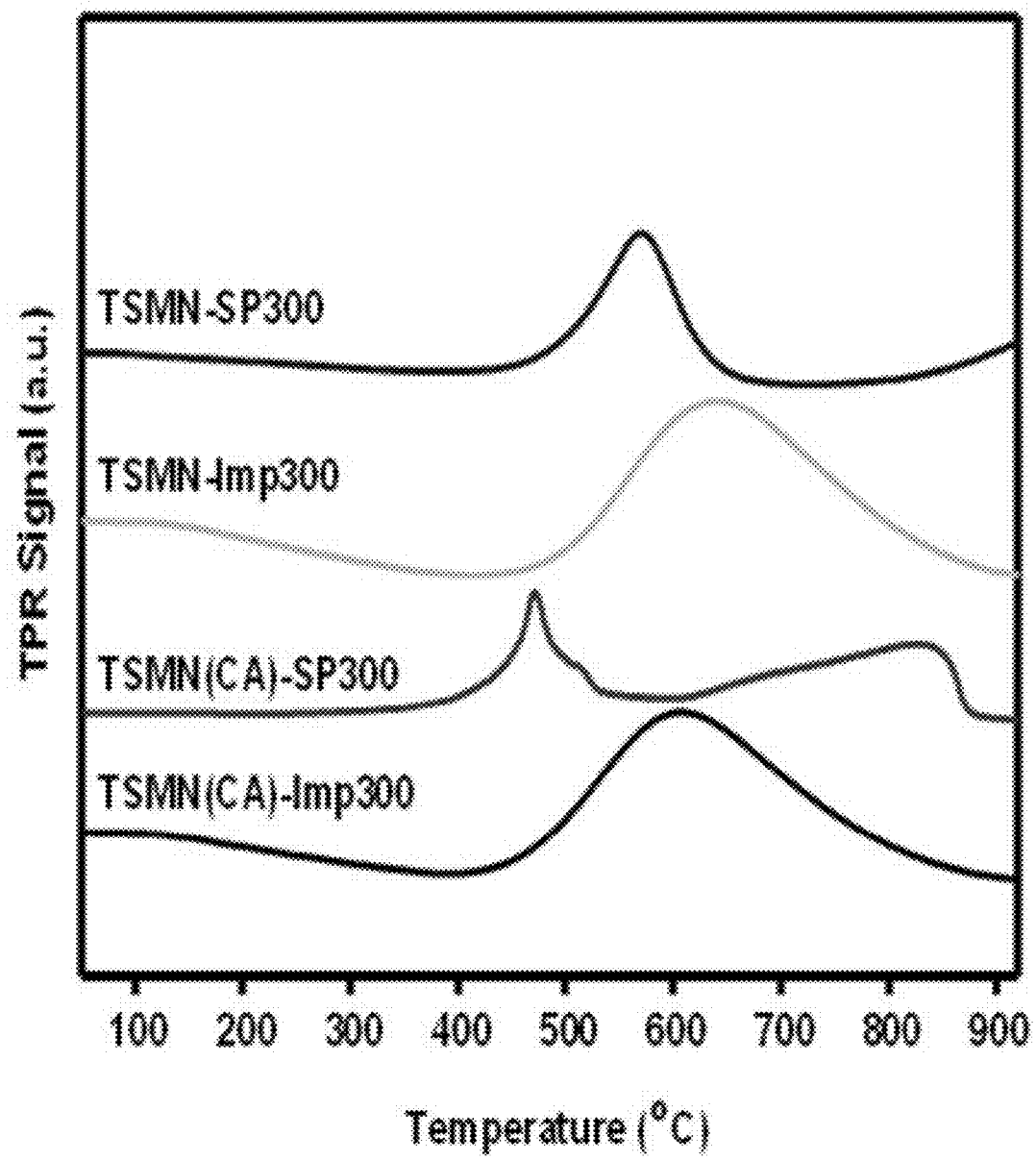
FIG. 14 represents the results of temperature-programmed reduction by hydrogen (TPR-H$_2$) for different HDS catalysts (in oxide form) calcined at 300° C.
Figure 15:
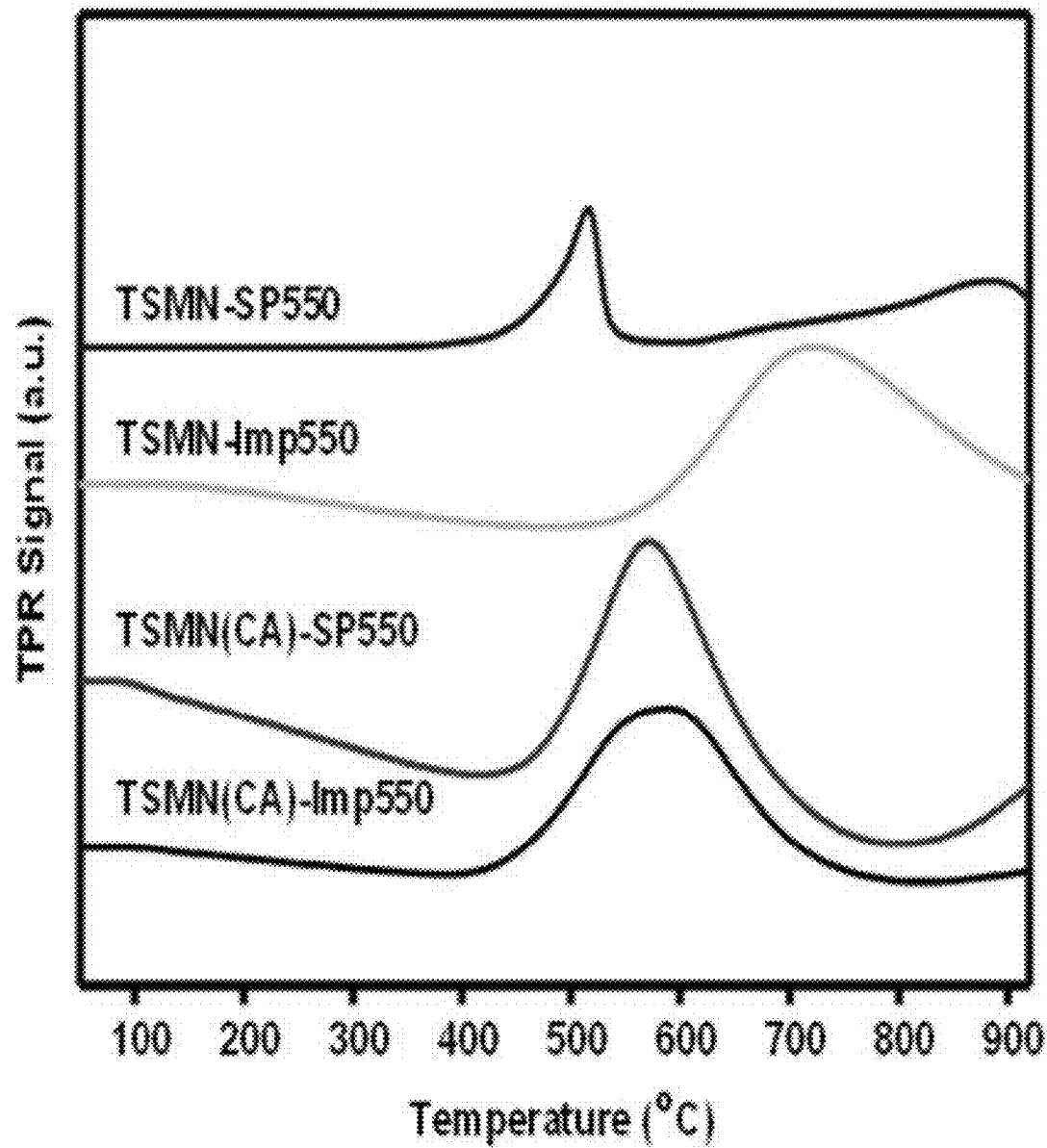
FIG. 15 represents the results of temperature-programmed reduction by hydrogen (TPR-H$_2$) for different HDS catalysts (in oxide form) calcined at 550° C.

FIG. 14 shows the temperature-programmed reduction by hydrogen ($H_2$-TPR) results of HDS catalysts prepared by the single-pot (SP) and impregnation approaches calcined at 300° C. FIG. 15 shows the temperature-programmed reduction by hydrogen ($H_2$-TPR) results of HDS catalysts prepared by the single-pot (SP) and impregnation approaches calcined at 550° C. A variation is noticed in the reduction temperature of the active metals (NiMo) due to either the active phase deposition method or calcination temperature. At relatively low temperature (450-650° C.) the main $H_2$ consumption temperature corresponding to the reduction of $Mo^{6+}$ to $Mo^{4+}$ is observed. The only exception is TSMN-Imp550, which shows strong metal-support interaction resulting in $Mo^{6+}$ to $Mo^{4+}$ reduction at a higher temperature (~720° C.).

The reduction temperatures for the catalysts prepared by impregnation are higher than those prepared by the single-pot (SP) approach. In addition, there is an appearance of a low-intensity $H_2$ consumption peak between 850° C. and 1000° C., which is characteristic of the reduction of monomeric molybdena in a single step from $Mo^{6+}$ to $Mo^0$ with reduced Mo in a tetrahedral arrangement. It has been reported that the increase in the reduction temperature is related to a strong metal support interaction, which decreases dispersion and in turn affects the catalytic performance. It is noteworthy that the use of citric acid (as a complexing agent) aids the dispersion of the active phase, as observed in the XRD and Raman spectrometry results; this was further established by the lower reduction temperature in the H2-TPR analysis. These results are in accord with the report by Badoga, et al., who used EDTA as a complexing agent.

Figure 18:
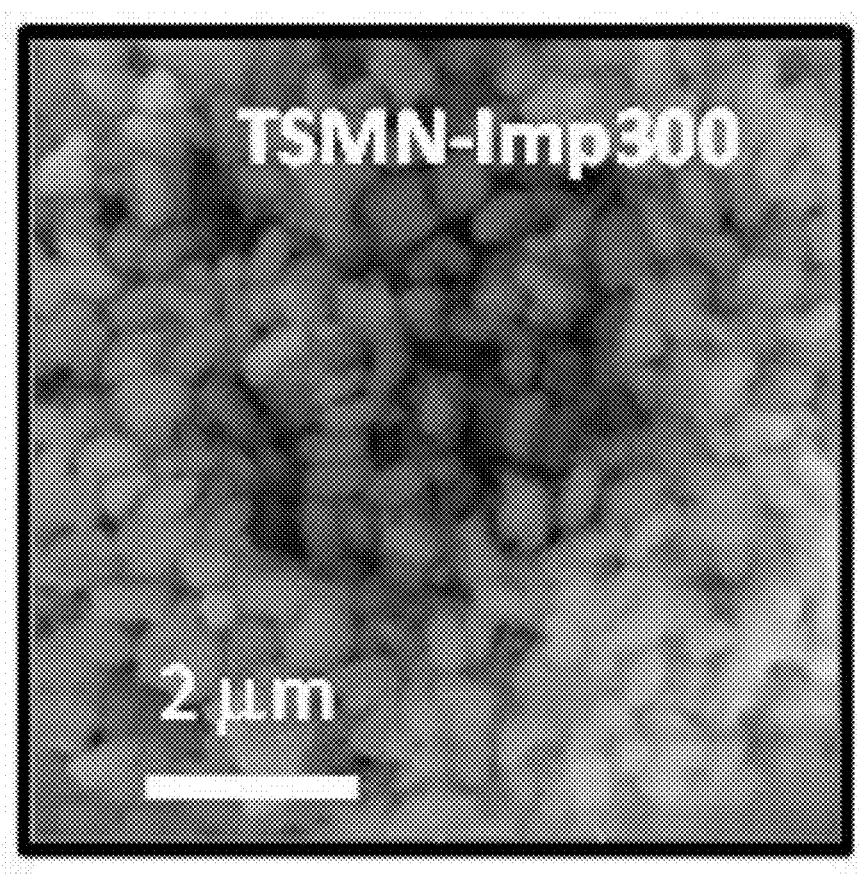
FIG. 18 is a SEM micrograph of the HDS catalyst that is produced via an impregnation method, calcined at 300° C.
Figure 19:
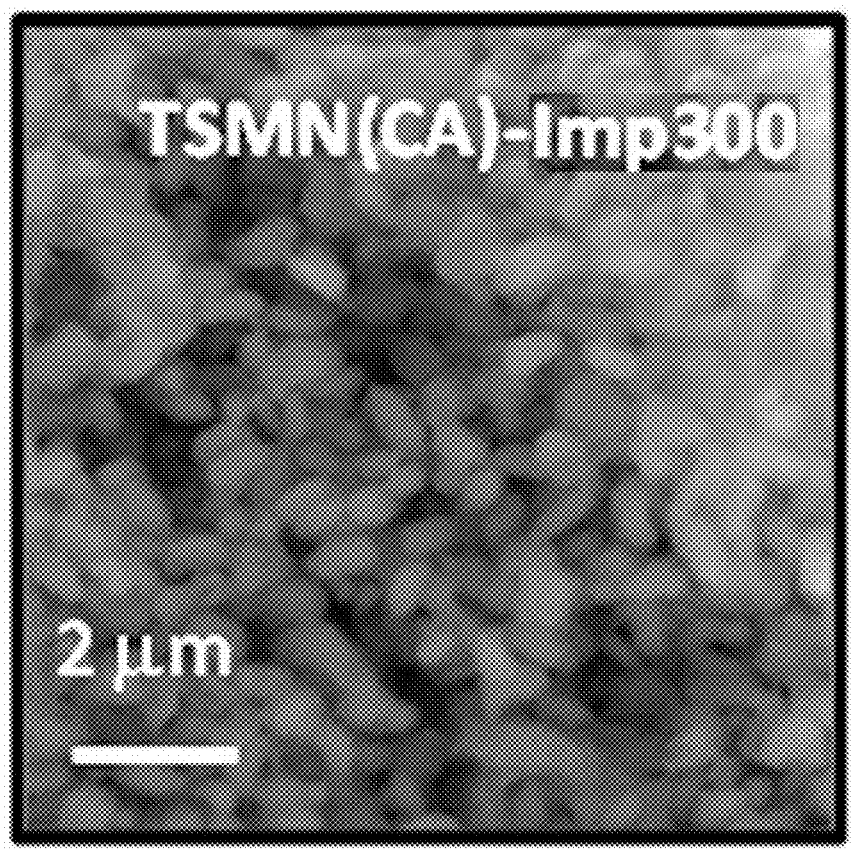
FIG. 19 is a SEM micrograph of the HDS catalyst that is produced via the impregnation method in the presence of a complexing agent, calcined at 300° C.
Figure 20:
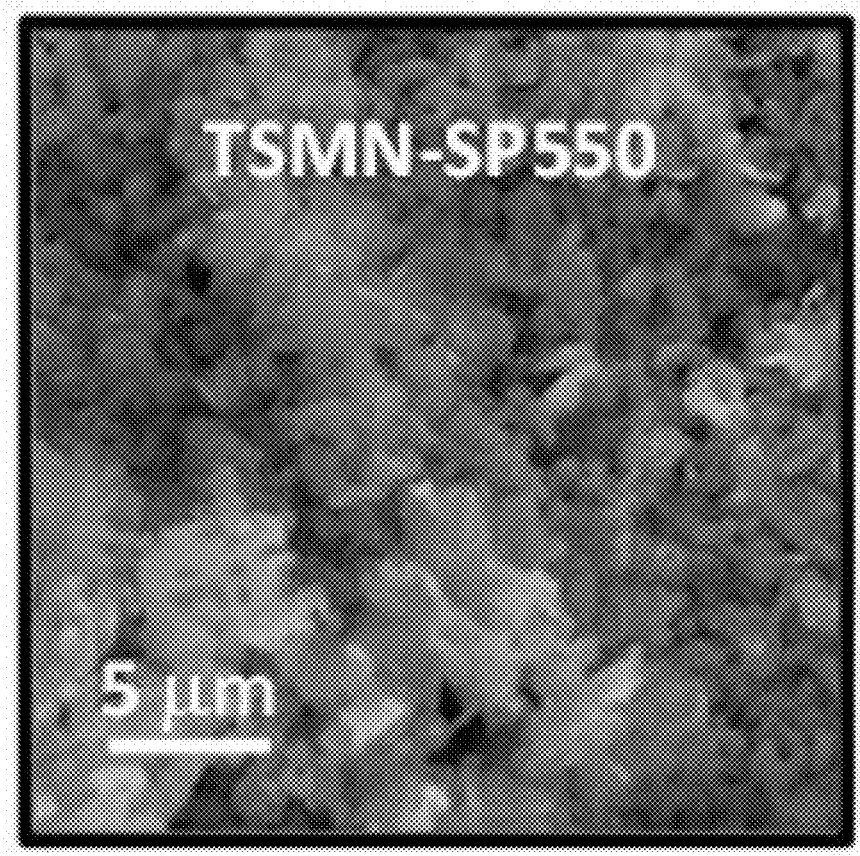
FIG. 20 is a SEM micrograph of the HDS catalyst that is produced via the single-pot method, calcined at 550° C.
Figure 21:
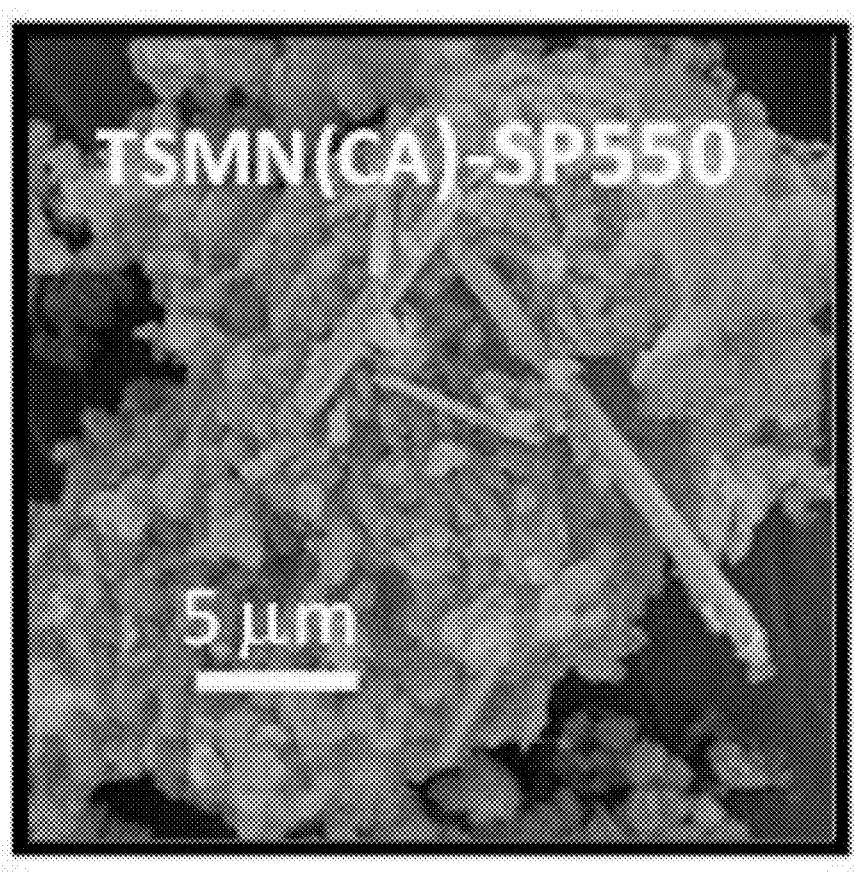
FIG. 21 is a SEM micrograph of the HDS catalyst that is produced via the single-pot method in the presence of a complexing agent, calcined at 550° C.
Figure 22:
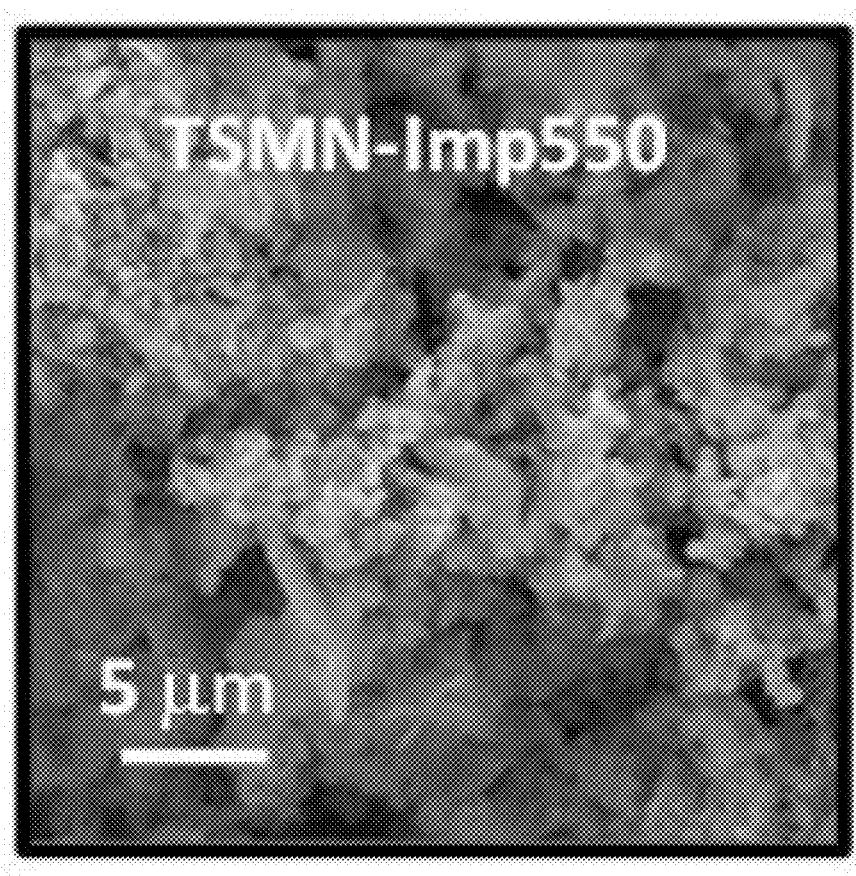
FIG. 22 is a SEM micrograph of the HDS catalyst that is produced via the impregnation method, calcined at 550° C.
Figure 23:
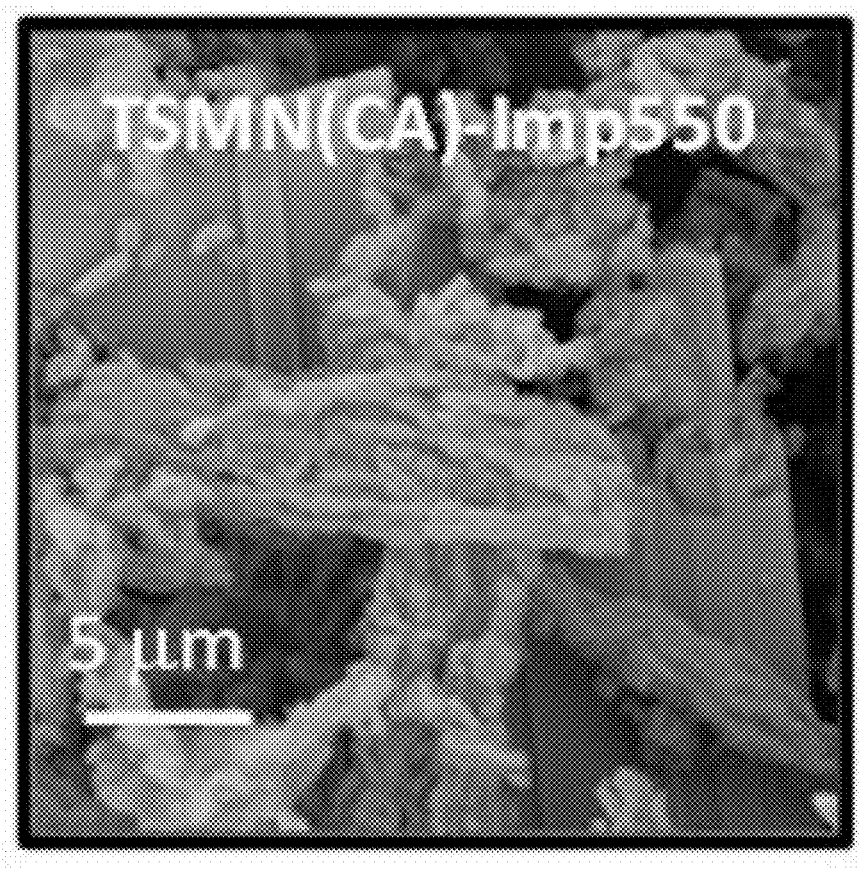
FIG. 23 is a SEM micrograph of the HDS catalyst that is produced via the impregnation method in the presence of a complexing agent, calcined at 550° C.

Example 10—Field Emission Scanning Electron Microscopy (FE-SEM) and Transmission Electron Microscopy (TEM) Analysis of the Synthesized Catalysts The TESCAN LYRA 3 unit was used to examine the morphology of SBA-15 and modified SBA-15-NiMo catalysts using secondary electron (SE) and backscattered electron (BSE) modes at an accelerating voltage of 30 kV. The unit was equipped with an energy-dispersive X-ray spectrometer (EDS, Oxford, Inc.) detector for elemental analysis. FIG. 16, FIG. 17, FIG. 18, FIG. 19, FIG. 20, FIG. 21, FIG. 22, and FIG. 23 present images captured by scanning electron microscopy for non-sulfided HDS catalysts. FIG. 16 shows a FESEM image result of the TSMN-SP300 catalyst as prepared. FIG. 17 shows a FESEM image result of the TSMN(CA)-SP300 catalyst as prepared. FIG. 18 shows a FESEM image result of the TSMN-Imp300 catalyst as prepared. FIG. 19 shows a FESEM image result of the TSMN(CA)-Imp300 catalyst as prepared. FIG. 20 shows a FESEM image result of the TSMN-SP550 catalyst as prepared. FIG. 21 shows a FESEM image result of the TSMN (CA)-SP550 catalyst as prepared. FIG. 22 shows a FESEM image result of the TSMN-Imp550 catalyst as prepared. FIG. 23 shows a FESEM image result of the TSMN(CA)-Imp550 catalyst as prepared.

For catalysts prepared by the single-pot (SP) approach (with or without citric acid) subjected to a low calcination temperature (300° C.), a unique nano-cubical flat-sheet morphology of Mo is observed, and this morphology is grown alongside the rod-like morphology of heteroatom modified-SBA-15. However, the low calcination temperature catalysts obtained by the impregnation method show little or no NiMo particles on the surface of the support, which indicates that active metals are preferably embedded in the SBA-15 structural unit. For all non-sulfided catalysts obtained at a high calcination temperature (550° C.), there are long rectangular rods of Mo on the support, which is responsible for the observed high-intensity crystalline phases of $MoO_3$. These results are in agreement with those obtained by Raman spectrometry and XRD analysis.

Figure 24:
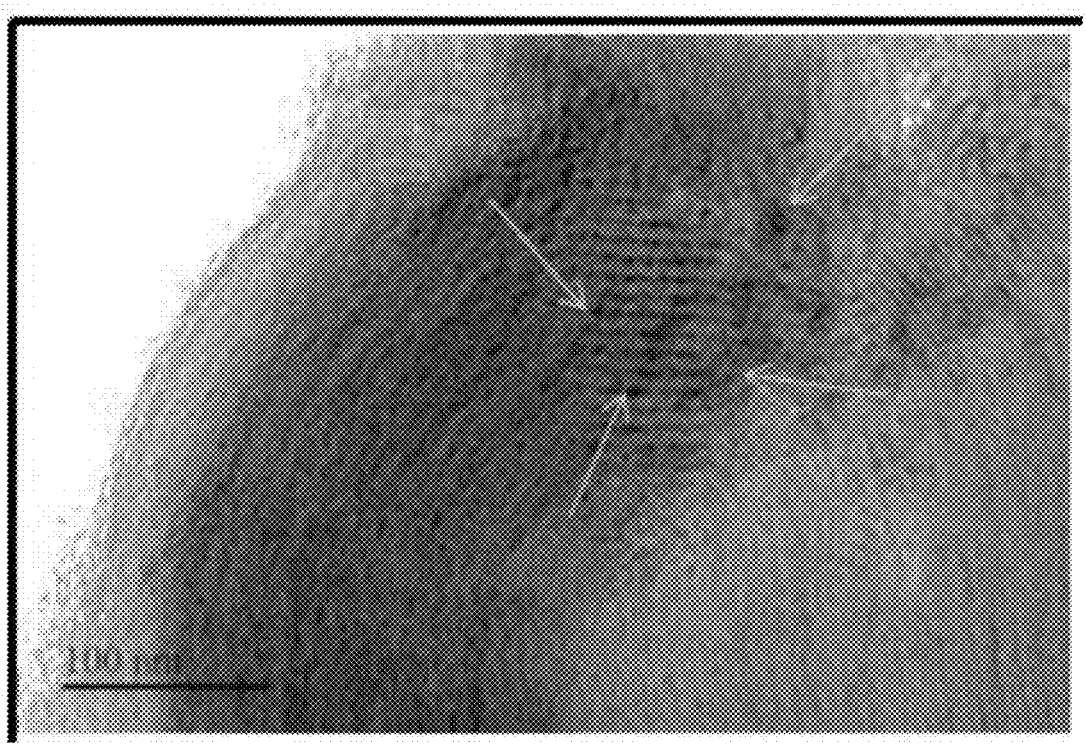
FIG. 24 is a TEM micrograph of the HDS catalyst that is produced via the single-pot method, calcined at 300° C.
Figure 25:
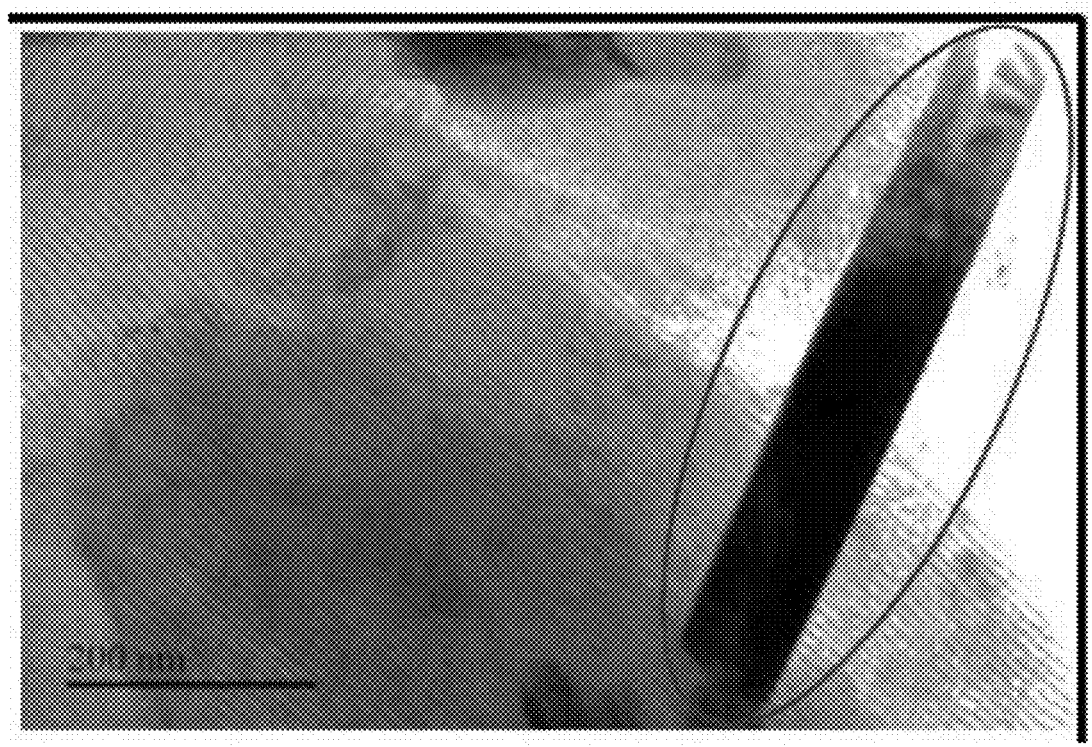
FIG. 25 is a TEM micrograph of the HDS catalyst that is produced via the single-pot method, calcined at 550° C.
Figure 26:
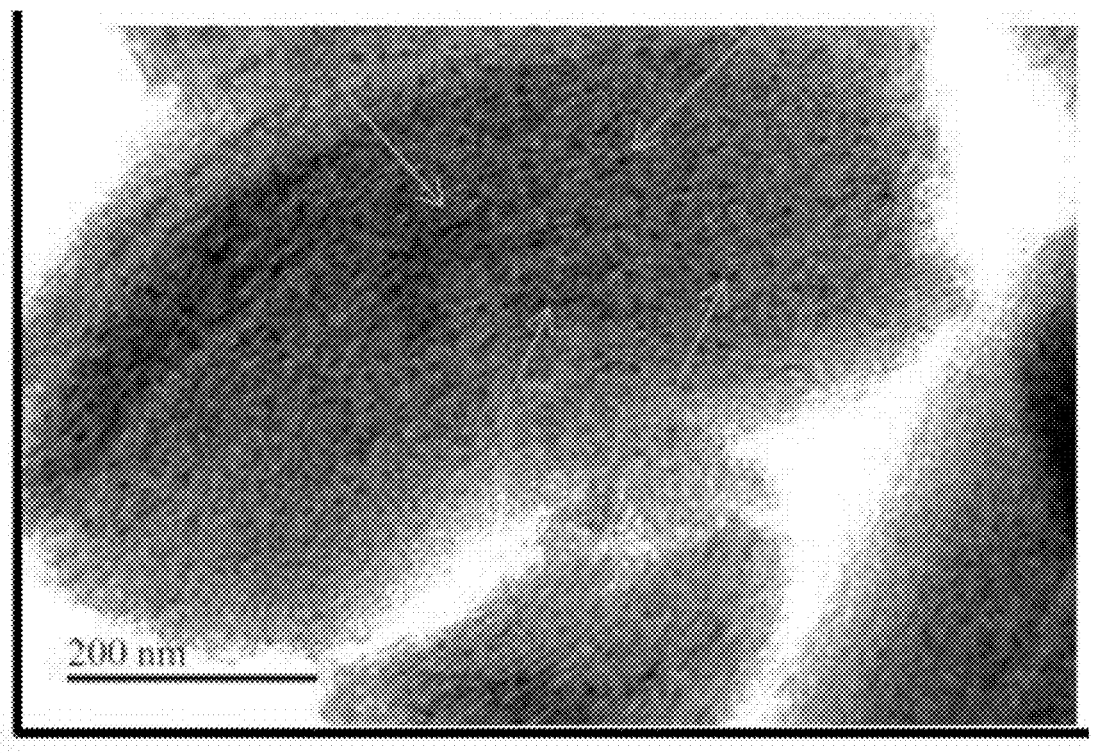
FIG. 26 is a TEM micrograph of the HDS catalyst that is produced via the impregnation method, calcined at 300° C.
Figure 27:
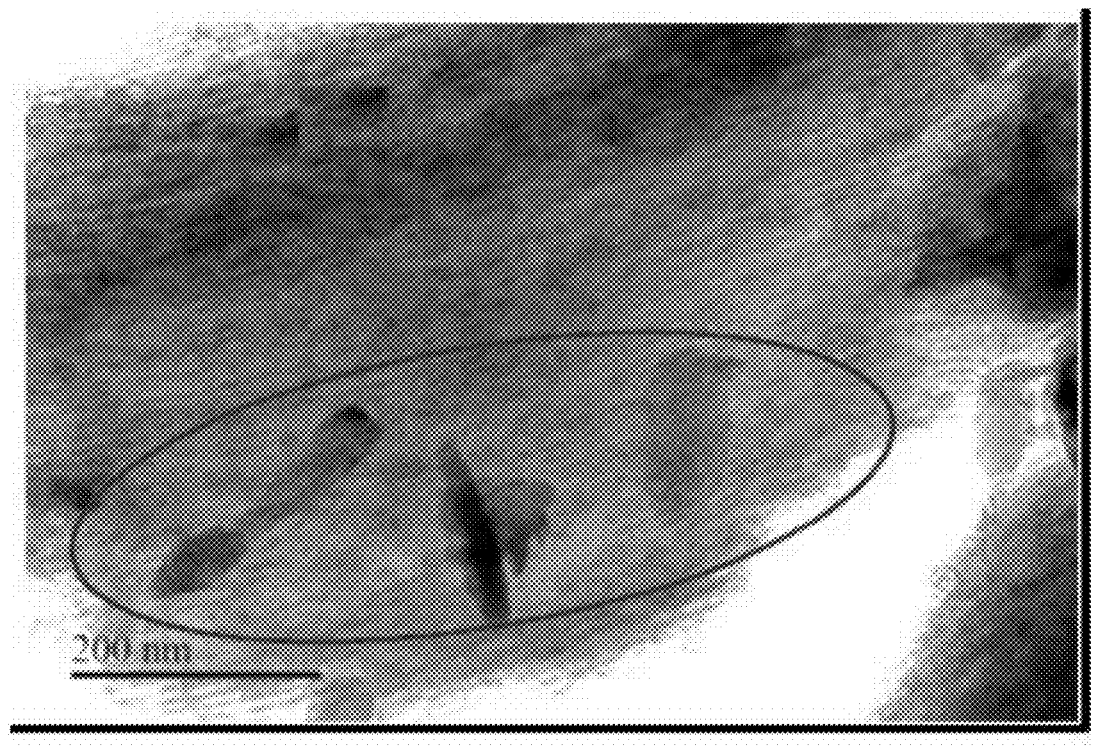
FIG. 27 is a TEM micrograph of the HDS catalyst that is produced via the impregnation method, calcined at 550° C.

TEM was used to confirm the metal dispersion in non-sulfided catalysts as a complimentary technique. Microstructural analysis of non-sulfided NiMo catalysts was performed on a JEOL JEM-2100F field emission electron microscope operated at 200 kV. The sample preparation was performed by dispersing ground power in ethanol until total dissolution, which was followed by deposition on a 3 mm copper grid coated with carbon for TEM analysis. FIG. 24 shows a TEM image analysis of the TSMN-SP300 catalyst as prepared. FIG. 25 shows a TEM image analysis of the TSMN-SP5500 catalyst as prepared. FIG. 26 shows a TEM image analysis of the TSMN-Imp300 catalyst as prepared. FIG. 27 shows a TEM image analysis of the TSMN-Imp550 catalyst as prepared. As shown in FIG. 24, FIG. 25, FIG. 26, and FIG. 27, the dispersion of active metal embedded within the Ti-SBA-matrix for catalyst calcined at 300° C. is confirmed by the minimal presence or lack of metal particle growth on the support, whereas the hexagonal microstructure of the SBA-15 framework is better preserved. In contrast, the presence of different sized rectangular rods is observed on the surface of the Ti-SBA-15 matrix for catalysts subjected to the higher calcination temperature (550° C.).

Example 11—Presulfiding and Performance Evaluation of the Synthesized Catalysts

Samples of prepared catalysts were pelletized, crushed, and sieved into 300-500 micron sizes. Each sample was reduced under a flow of 5% $H_2$/He (60 mL/min) at 400° C. (ramp rate of 10° C./min) for 2 hours to convert Ni and Mo to metallic forms. Presulfidation was performed using a solution containing 2 wt. % $CS_2$ in a quartz tube at 350° C.

The HDS performance of prepared catalysts was evaluated in a high-pressure batch reactor (model: Parr 4576B) at 350° C. under 5 MPa of $H_2$ pressure and constant 300 rpm stirring. Approximately 0.25 g of catalyst was added to 100 mL of the simulated feed containing dibenzothiopene (DBT) (2500 ppm-S) in dodecane. Each test was conducted for 4 hours after the target process conditions were achieved. Product samples were collected every hour during this period. The sulfur content in the feed a products was quantified using a gas chromatography sulfur chemiluminescence detector (GC-SD), and product identification was achieved with gas chromatography mass spectrometry (GC-MS). Hydrocarbon analysis was performed with a gas chromatography flame ionization detector (GC-FID).

Figure 28:
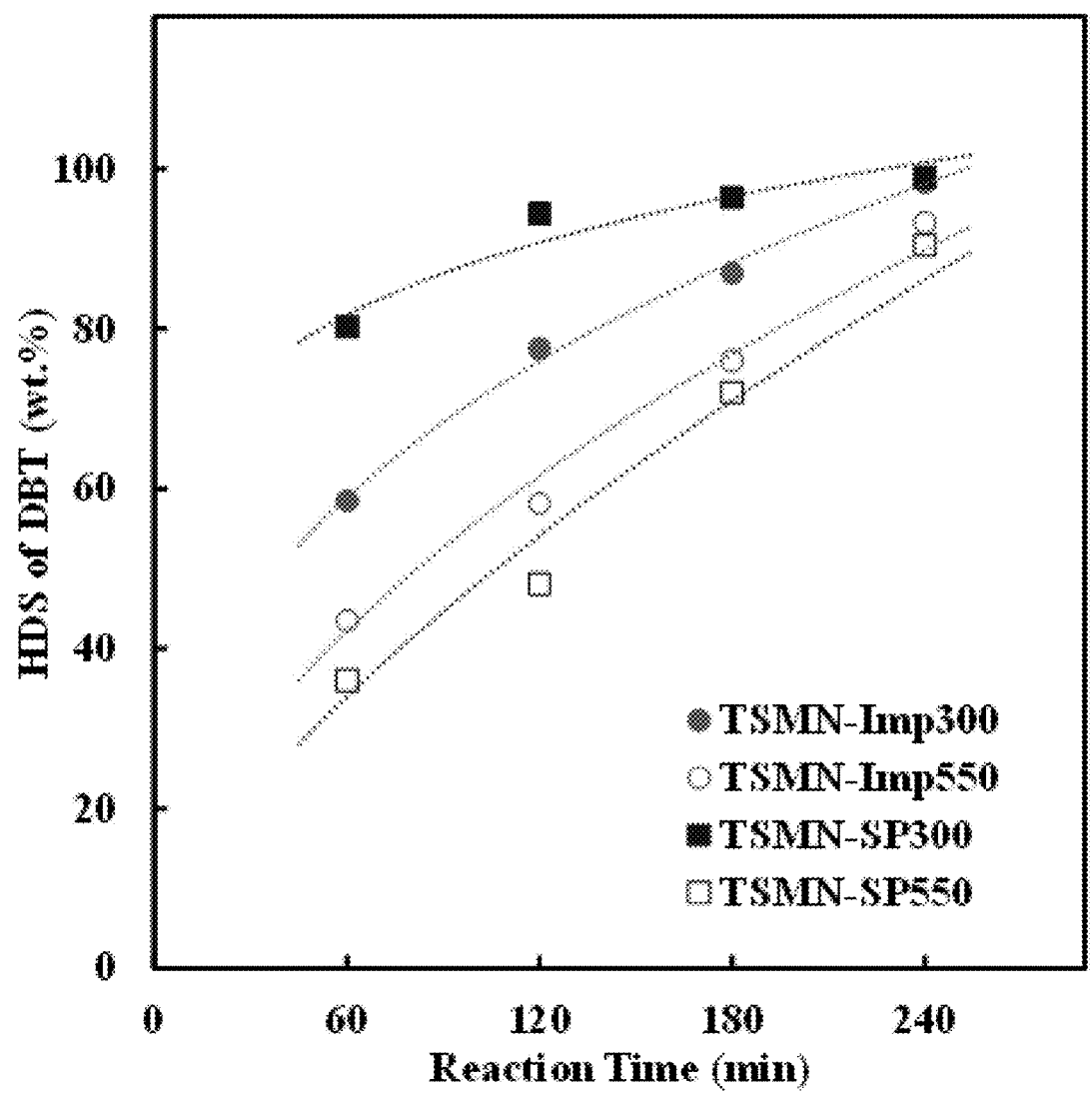
FIG. 28 represents activities of different HDS catalysts in hydro-desulfurizing dibenzothiophene at different contact times.

Performance evaluation of the synthesized catalysts was performed in a batch autoclave reactor using dibenzothiophene (DBT) as the model sulfur compound. The initial sulfur content of the reactant was 2500 ppm, and the process conditions were 350° C. and 5 MPa. Table 4 presents the sulfur contents of the products at different reaction times. The results shows a significant variation in the performance of the synthesized catalysts, which indicates the influence of the preparation method (single-pot versus impregnation), calcination temperature (300° C. versus 550° C.), and complexing agent. In terms of initial activity, which can be estimated by the product sulfur content after one hour, catalysts calcined at 300° C. perform better than those calcined at 500° C., irrespective of the preparation method or the use of a complexing agent. When the complexing agent is not used, the performance of the catalyst prepared by the SP method (TSMN-SP300) is significantly better than the catalyst prepared by the conventional impregnation method (TSMN-Imp 300). The trend of the initial activity is observed to be TSMN-SP300>TSMN-Imp300>TSMN-Imp550>TSMNSP550. This trend continues with increased reaction time, as shown in FIG. 28.

TABLE 4

Catalyst performance test results: product sulfur content.
(Process Conditions: 350° C.; 5 MPa; Reaction Time: 4 h;
Feed Sulfur Content = 2,500 ppm)

| Catalysts | Product Sulfur Content (ppm) | | | |
|---|---|---|---|---|
| | 1 h | 2 h | 3 h | 4 h |
| TSMN-Imp300 | 1,038 | 562 | 327 | 41 |
| TSMN-Imp550 | 1,411 | 1,046 | 600 | 168 |
| TSMN-SP300 | 494 | 139 | 90 | 25 |
| TSMN-SP550 | 1,600 | 1,300 | 700 | 238 |
| TSMN(CA)-Imp300 | 639 | 343 | 164 | 27 |
| TSMN(CA)-Imp550 | 1,349 | 702 | 443 | 37 |
| TSMN(CA)-SP300 | 763 | 600 | 295 | 34 |
| TSMN(CA)-SP550 | 1,377 | 889 | 529 | 247 |

Figure 29:
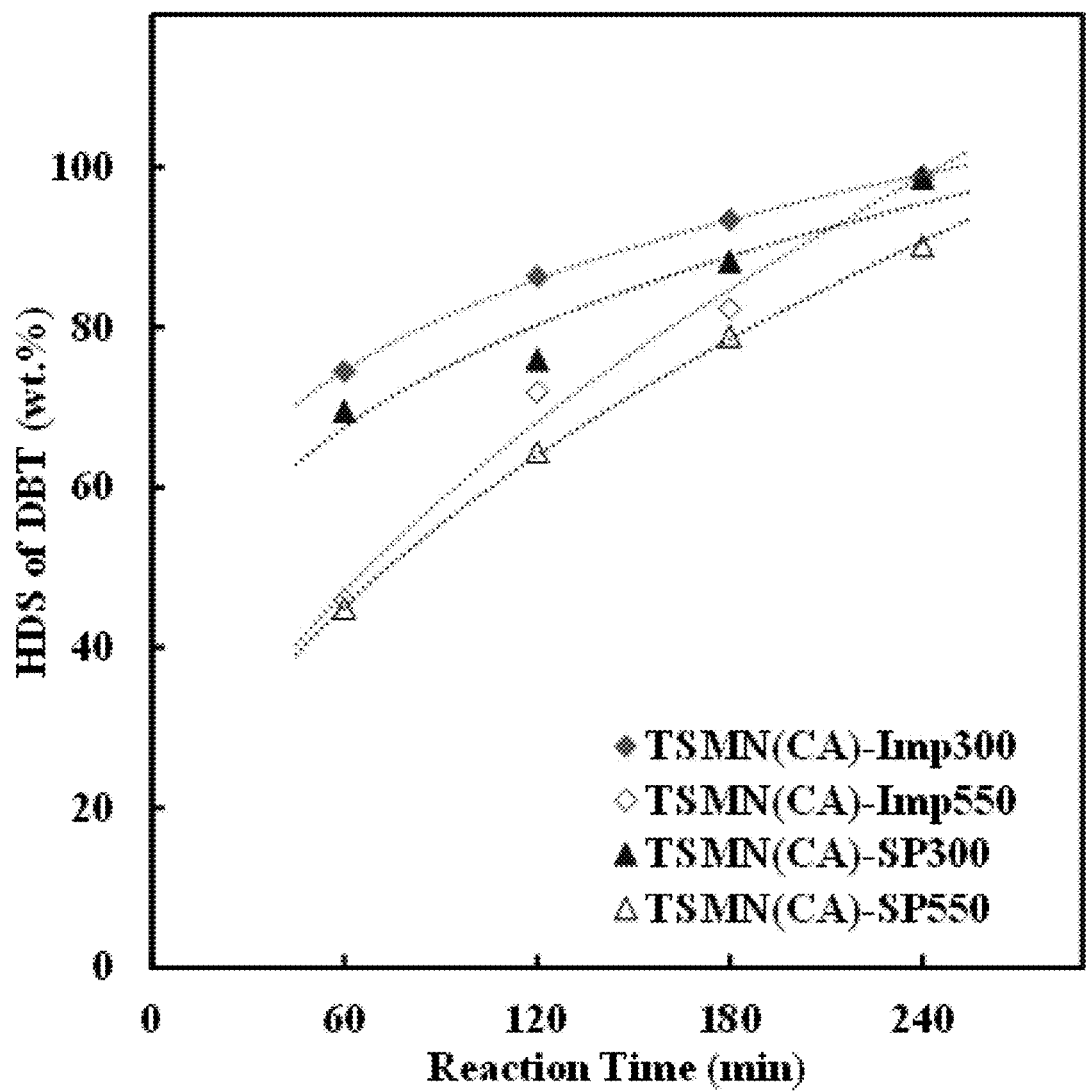
FIG. 29 represents activities of different HDS catalysts in hydro-desulfurizing dibenzothiophene at different contact times, wherein a complexing agent is used to produce the HDS catalysts.

For the catalysts prepared using the complexing agent, the influence of the preparation method (SP versus impregnation) is modest, but impregnation is better. However, the influence of calcination temperature remains significant. Thus, the trend in the initial activity is found to be TSMN(CA)-Imp300>TSMN(CA)-SP300>TSMN(CA)-Imp550~TSMN(CA)-SP550. With the increase in reaction time, however, the influence of calcination temperature also diminishes, as shown in FIG. 29.

Example 12—HDS Activity and Reaction Pathways

The HDS of DBT occurs via two parallel pathways as illustrated in FIG. 30: (i) direct desulfurization (DDS) or hydrogenolysis by C—S bond cleavage in a single step; or (ii) hydrogenation (HYD) in 2-3 steps through the hydrogenation of one of the phenyl rings followed by C—S bond cleavage [S. H. Moon, Catalysis Survey from Asia, 7 (2003) 11-20]. The HDS of DBT via the DDS pathway yields biphenyl (BP) and $H_2S$ as final products. However, the HYD pathway results in the formation of intermediates, such as tetrahydro dibenzothiophene (THDBT) and hexahydro dibenzothiophene (HHDBT), followed by fast desulfurization to form cyclohexyl benzene (CHB). Because the DDS pathway consumes substantially less hydrogen, it is the preferred route.

The analysis of hydrocarbon products obtained after one hour of reaction time over different synthesized catalysts is presented in Table 5. BP is the predominant compound in all products, indicating that DDS is the generally preferred route. However, there are significant differences in the preference for DDS among the synthesized catalysts as revealed by the BP/CHB ratio in the products. When a complexing agent is not used, the catalysts calcined at 300° C. exhibit approximately twice the BP/CHB ratio of catalysts calcined at 550° C. The catalysts prepared by the SP method and calcined at 300° C. show exceptional preference for the DDS route with a BP/CHB ratio of approximately 10. The use of a complexing agent significantly reduces the BP/CHB ratio, which indicates that the direct scission of the C—S bond is not effective and that the hydrogenation reaction is also enhanced. The effect of calcination temperature on the BP/CHB ratio is not significant when complexing is used.

The 4-HDBT intermediate is detected only in products obtained from TSMN-Imp550, TSMN-SP550, and TSMN (CA)-SP550. These are low-activity catalysts, which also result in higher sulfur contents (>150 ppm) in the products even after a contact time of 4 h (Table 4).

TABLE 5

Catalyst performance test results: product distribution.
(Process Conditions: 350° C.; 5 MPa; Reaction Time: 1 h)

| Catalysts | Product Distribution (wt. %) | | | BP/CHB |
|---|---|---|---|---|
| | CHB | BP | 4HDBT | |
| TSMN-Imp300 | 19.91 | 80.09 | — | 4.02 |
| TSMN-Imp550 | 31.61 | 61.72 | 6.67 | 1.95 |
| TSMN-SP300 | 9.12 | 90.89 | — | 9.97 |
| TSMN-SP550 | 14.63 | 76.42 | 8.95 | 5.22 |
| TSMN(CA)-Imp300 | 32.13 | 67.87 | — | 2.11 |
| TSMN(CA)-Imp550 | 28.52 | 71.48 | — | 2.51 |
| TSMN(CA)-SP300 | 14.70 | 85.30 | — | 5.80 |
| TSMN(CA)-SP550 | 14.94 | 76.49 | 8.57 | 5.12 |

Example 13—HDS Kinetics

The HDS rates were calculated assuming pseudo-first order kinetics, and the values of the reaction constant, k ($min^{-1}$), were determined using conversion values during the first hour of the reaction. The results presented in Table 6 show that the value of the HDS rate constant is $13.5 \times 10^{-3}$ $min^{-1}$ for the TSMN-Imp300 catalyst. This value compares well with the reported rate constant of $18.3 \times 10^{-3}$ $min^{-1}$ for the HDS of DBT at 350° C. over a $CoMo/Al_2O_3$ catalyst [S. A. All, S. Ahmed, K. W. Ahmed, M. A. Al-Saleh, Fuel Processing Technology 98 (2012) 39-44].

Effect of Calcination Temperature

The decrease in the calcination temperature from 550° C. to 300° C. results in consistently higher IDS rates. The catalyst prepared by the impregnation method without the complexing agent (TSMN-Imp550) exhibits an HDS rate of $8.4 \times 10^{-3}$ $min^{-1}$, which is increased by approximately 61% to $13.5 \times 10^{-3}$ $min^{-1}$ when the calcination temperature is reduced (TSMN-Imp300). The catalyst prepared by the SP method and calcined at 300° C. (TSMN-SP300) exhibits the highest rate constant of $25.6 \times 10^{-3}$ $min^{-1}$, which is approximately four times the rate obtained with TSMN-SP550. The trend of a higher HDS rate for the catalysts calcined at 300° C. is also observed for the catalysts prepared using a complexing agent. However, the increase is moderately higher for the catalysts prepared by the impregnation method (47%) compared with those prepared by the SP method (41%). It seems that the addition of a complexing agent offsets some of the benefits of a lower calcination temperature.

The rate constants for the DDS and HYD pathways are presented in Table 6 as $k_{DDS}$ and $k_{HYD}$, respectively. In addition to the significant increase in the HDS rates, a lower calcination temperature is effective in promoting HDS by the DDS pathway. The catalyst prepared by the impregnation method without the complexing agent (TSMN-Imp550) exhibits a $k_{DDS}/k_{HYD}$ ratio of 1.7, which is increased by three times when the calcination temperature is reduced (TSMN-Imp300). The catalyst prepared by the SP method and calcined at 300° C. (TSMN-SP300) exhibits the highest $k_{DDS}/k_{HYD}$ ratio of 17.2, which is approximately five times the rate obtained with TSMN-SP550. It should be noted that while $k_{DDS}$ increases four times due to a reduction in the calcination temperature, $k_{HYD}$ remains unchanged. This observation indicates that the active sites for DDS may be different from those in the HYD pathway.

The trend of a higher HDS rate for the catalysts calcined at 300° C. is also observed for the catalysts prepared by the SP method using a complexing agent. However, the increase is not as drastic as that observed with the catalysts prepared without the complexing agent.

As shown in Section 3.1, the catalyst prepared by the SP method and calcined at 300° C. (TSMN-SP300) possesses a significantly higher surface area (460 $m^2/g$) and pore volume (0.66 $cm^3/g$) compared to the catalyst calcined at 550° C. (TSMN-SP550). This method provides a much better dispersion of active metals and better accessibility to reactants. TSMN-SP300 also exhibits the highest surface acidity among the catalysts prepared without the addition of a complexing agent. XRD results also show that the catalysts calcined at 300° C. exhibit better dispersion of active metals on the support and the presence of small crystallites. Similar trends are observed by Raman spectrometry and FTIR spectroscopy. These factors can be attributed to the highest overall HDS rate of TSMN-SP300 as well as the increased DDS activity.

Effect of Preparation Method

Comparison of the HDS rates exhibited by catalysts prepared by the two methods investigated in this study, i.e., impregnation and SP, provides insight into the efficacy of each method. The SP approach presents new, simple, and easy steps in catalyst design and preparation, which leads to low-cost catalyst design and the incorporation of the active phase within the mesoporous framework. The catalyst prepared by the SP method exhibits higher HDS activity compared to catalyst prepared by impregnation when the calcination temperature is 300° C. The overall HDS rate constant of TSMN-SP300 is approximately 90% higher than the rate constant of TSMN-Imp300. Moreover, HDS by DDS is significantly enhanced by TSMN-SP300, resulting in a 3.5-fold increase in the $k_{DDS}/k_{HYD}$ ratio. However, when the calcination temperature is increased to 550° C., the catalyst prepared by the SP method exhibits lower activity, and the benefits of the SP method in terms of the $k_{DDS}/k_{HYD}$ ratio are drastically reduced.

The main differences in the characteristics of the catalysts prepared by the SP and impregnation methods are the significantly higher surface area (especially the macroporous surface area) and pore volume for SP catalysts. The catalysts prepared by the SP method also possess higher surface acidity, which can enhance C—S bond scission and result in higher DDS.

The use of a complexing agent improves the performance of catalysts prepared by the impregnation method. The increase in the HDS rate from TSMN-Imp 300 to TSMN (CA)-Imp300 is 46%. However, this improvement is reduced to only 24% when the calcination temperature is increased to 550° C. The use of a complexing agent affected the performance of catalysts prepared by the SP method in a different manner. Although the complexing agent is beneficial for the overall HDS rate when the calcination temperature is 550° C., it exhibits a negative impact at the calcination temperature of 300° C. However, the $k_{DDS}/k_{HYD}$ ratio of 8.3 for TSMN(CA)-SP300 is the highest among all catalysts prepared using a complexing agent.

Figure 31:
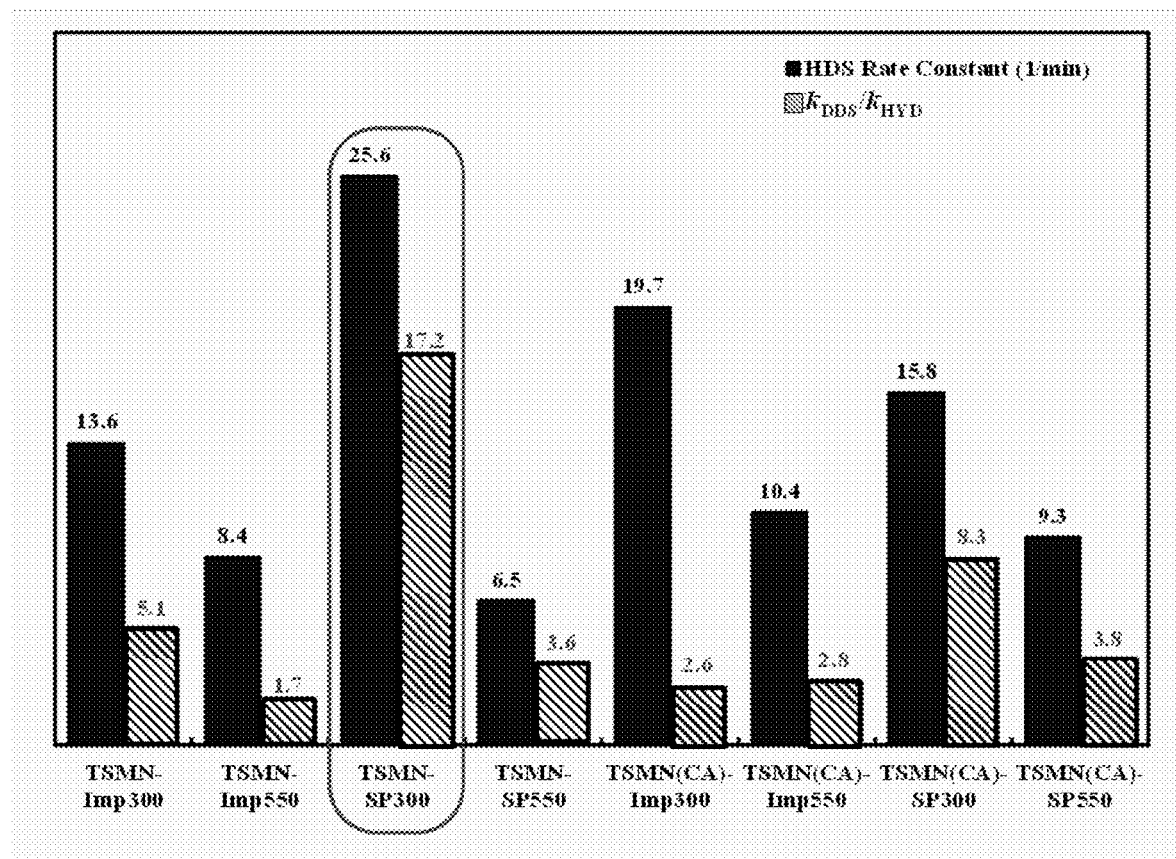
FIG. 31 represents hydrodesulfurization reaction rate constants and rate constant ratios, with respect to direct desulfurization (DDS), for different HDS catalysts.

The incorporation of a complexing agent improves the dispersion of active metals as observed by XRD and Raman spectrometry. The impact of better dispersion is evident from the improved HDS activity of catalysts prepared by the impregnation method, i.e., by comparing TSMN(CA)-Imp300 and TSMN(CA)-Imp550 to TSMN-Imp300 and TSMN-Imp550, respectively. However, the catalysts prepared by the SP method are negatively affected by the complexing agent. FIG. 31 represents hydrodesulfurization reaction rate constants and also rate constant ratios, with respect to direct desulfurization (DDS), for different HIDS catalysts that are investigated here.

In general, the HDS activities of the SP-approach catalysts at a low calcination temperature are better than the other catalysts within the series, and it is noteworthy that better performance could be achieved without the use of a complexing agent to aid the dispersion of active metals. Therefore, the preparation of supported HDS catalysts at a low calcination temperature leads to deep desulfurization within a short period of time due to high dispersion of the active phase, as indicated by the absence of crystalline phases in Raman spectrometry and XRD analyses.

TABLE 6

First-order rate constants for HDS of DBT at 350° C.

| Catalysts | $k_{HDS} \times 10^3$ (min$^{-1}$) | $k_{DDS} \times 10^3$ (min$^{-1}$) | $k_{HYD} \times 10^3$ (min$^{-1}$) | $k_{DDS}/k_{HYD}$ |
|---|---|---|---|---|
| TSMN-Imp300 | 13.6 | 10.5 | 2.1 | 5.1 |
| TSMN-Imp550 | 8.4 | 5.2 | 3.0 | 1.7 |
| TSMN-SP300 | 25.6 | 21.8 | 1.4 | 17.2 |
| TSMN-SP550 | 6.5 | 5.4 | 1.5 | 3.6 |
| TSMN(CA)-Imp300 | 19.7 | 11.7 | 4.6 | 2.6 |
| TSMN(CA)-Imp550 | 10.4 | 6.7 | 2.4 | 2.8 |
| TSMN(CA)-SP300 | 15.8 | 15.0 | 1.8 | 8.3 |
| TSMN(CA)-SP550 | 9.3 | 7.0 | 1.9 | 3.8 |

The single-pot (SP) synthesis of NiMo-supported Ti-SBA-15 HDS catalyst was successfully developed, and the catalyst was evaluated for the HDS of dibenzothiophene. The results with this catalyst were compared with those using the established impregnation approach. The catalyst from the SP approach exhibited a great potential to minimize the time involved in catalyst design and preparation. Furthermore, the use of a complexing agent to improve dispersion and prevent the formation of crystalline $NiMoO_4$ was optional. Overall, the SP catalyst formed at a low calcination temperature (TSMN-SP300) possessed superior catalytic performance and selectivity for direct desulfurization compared with the other studied catalysts.

The invention claimed is:

1. A method of producing a hydrodesulfurization catalyst, comprising:
   hydrothermally treating a hydrothermal precursor comprising a silica source, a structural directing surfactant, an aqueous acid solution, a first metal precursor, and a second metal precursor, to form the hydrodesulfurization catalyst,
   wherein each of the first and the second metal precursors comprises an active catalyst material selected from groups 4 to 12 of the periodic table, and
   wherein the hydrodesulfurization catalyst comprises at least two active catalyst materials deposited on a catalyst support comprising SBA-15.

2. The method of claim 1, further comprising:
   calcining the hydrodesulfurization catalyst at a temperature in the range of 200 to 650° C.

3. The method of claim 2, wherein the hydrodesulfurization catalyst is calcined at a temperature in the range of 250 to 350° C. for 2 to 12 hours.

4. The method of claim 1, wherein the hydrothermal precursor further comprises a titanium source, and wherein the catalyst support further comprises titanium.

5. The method of claim 1, wherein the hydrothermal precursor does not include a complexing agent.

6. The method of claim 1, wherein the hydrothermal precursor further comprises a complexing agent comprising citric acid.

7. The method of claim 1,
   wherein the first metal precursor comprises an active catalyst material selected from nickel and cobalt, and
   wherein the second metal precursor comprises an active catalyst material selected from molybdenum and tungsten.

8. The method of claim 7, wherein the first metal precursor is nickel nitrate and the second metal precursor is ammonium molybdate.

9. The method of claim 8, wherein a weight ratio of molybdenum to nickel in the hydrothermal precursor is in the range of 2:1 to 8:1.

10. The method of claim 1, wherein the hydrothermal precursor is formed by:
    mixing the structural directing surfactant with the aqueous acid solution to form an acid-surfactant solution and stirring the acid-surfactant solution for at least 30 minutes;
    mixing the acid-surfactant solution with the silica source to form a catalyst support mixture and stirring the catalyst support mixture for at least 20 hours; and
    mixing the catalyst support mixture with the first and the second metal precursors.

11. The method of claim 10, wherein the hydrothermal precursor further comprises a titanium source, the method further comprising:
    mixing the titanium source with the catalyst support mixture prior to mixing the catalyst support mixture with the first and the second metal precursors.

12. The method of claim 4, wherein a molar ratio of silicon in the silica source to the titanium in the titanium source is in the range of 5:1 to 20:1.

13. The method of claim 4, wherein the silica source is a tetraalkyl orthosilicate, and the titanium source is a titanium alkoxide.

14. The method of claim 4, wherein the silica source is tetraethyl orthosilicate, and the titanium source is titanium isopropoxide.

15. The method of claim 1, wherein the structural directing surfactant is a triblock copolymer comprising poly(ethylene oxide) and poly(propylene oxide).

* * * * *